United States Patent
Williams

(10) Patent No.: US 7,410,761 B2
(45) Date of Patent: *Aug. 12, 2008

(54) SYSTEM FOR RAPID IDENTIFICATION AND SELECTION OF NUCLEIC ACIDS AND POLYPEPTIDES, AND METHOD THEREOF

(75) Inventor: Richard B. Williams, South Pasadena, CA (US)

(73) Assignee: ProteoNova, Inc., Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/847,087

(22) Filed: May 17, 2004

(65) Prior Publication Data

US 2004/0229270 A1 Nov. 18, 2004

Related U.S. Application Data

(63) Continuation-in-part of application No. PCT/US02/37103, filed on Nov. 18, 2002, and a continuation-in-part of application No. 09/859,809, filed on May 17, 2001, now Pat. No. 6,962,781.

(60) Provisional application No. 60/529,331, filed on Dec. 12, 2003, provisional application No. 60/346,965, filed on Nov. 16, 2001, provisional application No. 60/206,016, filed on May 19, 2000.

(51) Int. Cl.
C12Q 1/68 (2006.01)
C12N 15/11 (2006.01)

(52) U.S. Cl. .......................................... 435/6; 536/23.1

(58) Field of Classification Search ....................... None
See application file for complete search history.

(56) References Cited

U.S. PATENT DOCUMENTS

| | | | |
|---|---|---|---|
| 4,599,303 | A | 7/1986 | Yabusaki et al. |
| 5,462,733 | A | 10/1995 | Edelson et al. |
| 5,688,670 | A | 11/1997 | Szostak et al. |
| 5,843,701 | A | 12/1998 | Gold et al. |
| 6,194,550 | B1 * | 2/2001 | Gold et al. .................. 530/358 |
| 6,207,446 | B1 | 3/2001 | Szostak et al. |
| 6,214,553 | B1 | 4/2001 | Szostak et al. |
| 6,261,804 | B1 | 7/2001 | Szostak et al. |
| 6,416,950 | B1 | 7/2002 | Lohse et al. |
| 6,429,300 | B1 | 8/2002 | Kurz et al. |
| 6,440,695 | B1 | 8/2002 | Merryman et al. |
| 6,602,685 | B1 | 8/2003 | Lohse |
| 6,623,926 | B1 | 9/2003 | Lohse et al. |
| 6,660,473 | B1 | 12/2003 | Lohse et al. |
| 2003/0022213 | A1 | 1/2003 | Merryman et al. |
| 2004/0038273 | A1 | 2/2004 | Merryman et al. |

FOREIGN PATENT DOCUMENTS

| EP | WO 92/02536 | 2/1992 |
|---|---|---|
| WO | WO 98/31700 | 7/1998 |
| WO | WO 99/51773 | 10/1999 |

OTHER PUBLICATIONS

Larry C. Mattheakis et al., *An in vitro polysome display system for identifying ligands from very large peptide libraries*, Proc. Natl. Acad. Sci. USA, vol. 91, pp. 9022-9026, Sep. 1994.

Jean-Pierre Bachellerie et al., *Identification of the modified nucleotides produced by covalent photoaddition of hydromethyltrimethylpsoralen to RNA*, Nucleic Acids Research, Nov. 9, 1981, vol. 9, pp. 2207-2222.

William R. Kobetz and John M. Essignmann, *Solid-Phase Synthesis of Oligonucleotides Containing A Site-Specific Psoralen Derivative*, American Chemical Society, Jan. 30, 1997, vol. 119, pp. 5960-5961.

William R. Kobetz and John M. Essignmann, *An Efficient Synthesis of a Furan-Side Furocoumarin Thymidline Monoadduct*, J. Org. Chem., 1997, vol. 62, pp. 2630-2632.

T. Martin Schmeing et al., *A pre-translocational intermediate in protein synthesis observed in crystals of enzymatically active 50S subunits*. Nature Structural Biology, Mar. 2002, vol. 9, No. 3, pp. 225-230.

Sambrook et al., *Molecular Cloning, a Laboratory Manual*. Cold Spring Harbor Laboratory Press, pp. 8.46-8.453, and 13.3-13.18, 1989.

Demeshkina, Natalia, et al., *Nucleotides of 18S rRNA surrounding mRNA codons at the human ribosomal A, P, and E sites: A crosslinking study with mRNA analogs carrying an aryl azide group at either the uracil or the guanine residue*. RNA (2000), 6: 1727-1736, Cambridge University Press.

Favre, Alain et al., *Thionucleobases as intrinsic photoaffinity probes of nucleic acid structure and nucleic acid-protein interactions*. Journal of Photochemistry and Photobiology B: Biology 42 (1998) pp. 109-124.

H. Bazin, X-X. Zhou, C. Glemarec and J. Chattopadhyaya, *Tetrahedron Letters*, vol. 28, No. 28, pp. 3275-3278, 1987, "An Efficient Synthesis of Y-Nucleoside (Wyosine) by Regiospecific Methylation of $N^4$-Desmethylwyosine Using Organozinc Reagent."

(Continued)

*Primary Examiner*—Nancy Vogel
(74) *Attorney, Agent, or Firm*—Knobbe, Martens, Olson & Bear, LLP

(57) ABSTRACT

This invention relates generally to systems and methods for identifying and selecting, desired proteins or nucleic acid molecules by linking mRNA, with known or unknown sequences, to its translated protein to form a cognate pair. The cognate pair is selected based upon desired properties of the protein or the nucleic acid. This method also includes the evolution of a desired protein or nucleic acid molecule by amplifying the nucleic acid portion of the selected cognate pair, introducing variation into the nucleic acid, translating the nucleic acid, attaching the nucleic acid to its protein to form a second cognate pair, and re-selecting this cognate pair based upon desired properties. Modified MRNAs operable to crosslink to tRNAs are also provided. Methods of producing a psoralen monoadduct or a crosslink are also provided.

4 Claims, 6 Drawing Sheets

OTHER PUBLICATIONS

"The -C-C-A End of tRNA and its Role in Protein Biosynthesis." Mathias Sprinzl and Friedrich Cramer; Progress in Nucleic Acid Research and Molecular Biology, vol. 22, 1979; pp. 1-69.

"Synthesis and Aminoacylation of 3'-Amino-3'-deoxy Transfer RNA and its Activity in Ribosomal Protein Synthesis." Thomas H. Fraser and Alexander Rich; Proceedings of the National Academy of Sciences of the United States of America, vol. 70, No. 9, pp. 2671-2675, Sep. 1973.

"Psoralens as Photoactive Probes of Nucleic Acid Structure and Function: Organic Chemistry, Photochemistry, and Biochemistry." George D. Cimino, et al.; Annual Review of Biochemistry, vol. 54, pp. 1151-1193, 1985.

"The Excitation of 8-Methoxypsoralen with Visible Light: Reversed Phase HPLC Quantitation of Monoadducts and Cross-Links." Francis P. Gasparro, et al.; Photochemistry and Photobiology, vol. 57, No. 6, pp. 1007-1010, 1993.

"Thionucleobases as Intrinsic Photoaffinity Probes of Nucleic Acid Structure and Nucleic Acid-Protein Interactions." Alain Favre, et al.; Journal of Photochemistry and Photobiology B: Biology, vol. 42, pp. 109-124, 1998.

"Spectroscopy and Photochemistry of Thiouracils: Implications for the Mechanism of Photocrosslinking in tRNA." Steven J. Milder and David S. Kliger; Journal of the American Chemical Society, vol. 107, pp. 7365-7373, 1985.

"The structure of a pre-mRNA molecule in solution determined with a site directed cross-linking reagent." John Teare and Paul Wollenzien; Nucleic Acids Research, vol. 18, No. 4, pp. 855-864.

"Mechanism of Growth Delay Induced in *Escherichia coli* by near Ultraviolet Radiation"; T.V. Ramabhadran, and J. Jagger; PNAS 1976; 73; 59-63.

"Enzymatic conversion of guanosine 3' adjacent to the anticodon of yeast tRNA phe to N-methylguanosine and the wye nucleoside: dependence on the anticodon sequence"; The EMBO Journal, vol. 6, No. 2, pp. 447-483, 1987.

"Comparison of Initiation of Protein Synthesis in Procaryotes, Eucaryotes, and Organelles"; Marilyn Kozak; Microbiological Reviews, Mar. 1983, p. 1-45, vol. 47, No. 1.

"A Bifunctional tRNA for In Vitro Selection"; Chuck Merryman, et al.; Chemistry & Biology, vol. 9, 741-746, Jun. 2002.

"Mechanism of Translocation: Relative Arrangement of tRNA and mRNA on the Ribosome"; Antonius J.M. Matzke, Andrea Barta and Ernst Kuechler; PNAS 1980; 77; 5110-5114.

"Specificity of Elongation Factor Tu from *Escherichia coli* with Respect to Attachment of the Amino Acid to the 2' or 3'-Hydroxyl Group of the Terminal Adenosine of tRNA"; Mathias Sprinzl, et al.; Eur. J. Biochem 78, 55-61 (1977).

"Joining of RNA Molecules with RNA Ligase"; Paul J. Romaniuk, et al., Methods in Enzymology, vol. 100, pp. 52-59.

"Photochemical properties of Y base in aqueous solution"; S. Paszyc, et al., Nucleic Acids Research, vol. 6, No. 1, Jan. 1979, pp. 385-398.

Utilizations of Various Uridine 5'-Triphosphate Analogues by DNA-Dependent RNA Polymerases I and II Purified from Liver Nuclei of the Cherry Salmon (*Oncorhynchus masou*); Chikao Nakayama and Mineo Saneyoshi; J. Biochem, 96, 1501-1509 (1984).

Properties of Alanyl-Oligonucleotide, Puromycin, and *Staphylococcus epidermidis* Glycyl-tRNA in Interaction with Elongation Factor Tu:GTP Complex; Makoto Kawakami, Shozo Tanada and Shosuke Takemura, FEBS Letters, vol. 51, No. 1, Mar. 1975.

"Measuring the extent of activation with [H]tryptophan by tryptophanyl-tRNA synthetase, relative to an untreated control"; Thomas H. Fraser, et al., Methods in Enzymology 59, pp. 134-145.

"Crosslinking transfer RNA and messenger RNA at the ribosomal decoding region: identification of the site of reaction on the messenger RNA"; Steiner et al., vol. 12, No. 21 (1984), Nucleic Acids Research, pp. 8181-8192.

"Compilation of tRNA sequences and sequences of tRNA genes"; Mathias Sprinzl, Konstantin S. Vassilenko, Sep. 2004 edition (4 pages); http://www.uni-bayreuth.de/departments/biochemie/trna.

Office Action dated Dec. 8, 2006 for U.S. Appl. No. 10/960,453.

Office Action dated Feb. 22, 2007 for U.S. Appl. No. 10/847,484.

* cited by examiner

FIG. 6

|  | Stable Acceptor | Native Esterified Acceptor |
|---|---|---|
| *Crosslinker on tRNA (Anticodon Loop)* | Example: SATA – Puromycin on tRNA and Crosslinker on tRNA<br><br>Crosslinker<br><br>Puromycin | Example: Linking tRNA Analog – Crosslinker on tRNA, but no puromycin<br><br>Crosslinker |
| *Crosslinker on mRNA (Message)* | Example: SATA – Puromycin on tRNA, Crosslinker on mRNA<br><br>Puromycin | Example: Nonsense Suppressor tRNA – Crosslinker on mRNA, no puromycin |

SEQUENCE LISTING

<160> NUMBER OF SEQ ID NOS: 32

<210> SEQ ID NO 1
<211> LENGTH: 13
<212> TYPE: RNA
<213> ORGANISM: Artificial Sequence
<220> FEATURE:
<223> OTHER INFORMATION: Precursor RNA for formation of psoralentated
      RNA; chemically synthesized fragment
<220> FEATURE:
<221> NAME/KEY: modified_base
<222> LOCATION: (6)...(6)
<223> OTHER INFORMATION: n=p

<400> SEQUENCE: 1
cuagancugg agg                                                          13

<210> SEQ ID NO 2
<211> LENGTH: 13
<212> TYPE: RNA
<213> ORGANISM: Artificial Sequence
<220> FEATURE:
<223> OTHER INFORMATION: Furan sided psoralentated RNA fragment;
      chemically synthesized
<220> FEATURE:
<221> NAME/KEY: misc_feature
<222> LOCATION: (2)...(3)
<223> OTHER INFORMATION: psoralen bound to UA
<220> FEATURE:
<221> NAME/KEY: modified_base
<222> LOCATION: (6)...(6)
<223> OTHER INFORMATION: n=p

<400> SEQUENCE: 2
cuagancugg agg                                                          13

<210> SEQ ID NO 3
<211> LENGTH: 23
<212> TYPE: RNA
<213> ORGANISM: Artificial Sequence
<220> FEATURE:
<223> OTHER INFORMATION: Chemically synthesized precursor RNA for
      psoralentated RNA fragment
<220> FEATURE:
<221> NAME/KEY: misc_feature
<222> LOCATION: (1)...(5)
<223> OTHER INFORMATION: n=g, a, u, or c
<220> FEATURE:
<221> NAME/KEY: misc_feature
<222> LOCATION: (19)...(23)
<223> OTHER INFORMATION: n=g, a, u, or c

<400> SEQUENCE: 3
nnnnnccucc agaucuagnn nnn                                               23

<210> SEQ ID NO 4
<211> LENGTH: 23
<212> TYPE: RNA
<213> ORGANISM: Artificial Sequence
<220> FEATURE:
<223> OTHER INFORMATION: Chemically synthesized psoralentated RNA
      fragment
<220> FEATURE:
<221> NAME/KEY: misc_feature
<222> LOCATION: (16)...(17)
<223> OTHER INFORMATION: psoralen bound to UA
<220> FEATURE:
<221> NAME/KEY: misc_feature
<222> LOCATION: (1)...(5)
<223> OTHER INFORMATION: n=g, a, u, or c

```
<220> FEATURE:
<221> NAME/KEY: misc_feature
<222> LOCATION: (19)...(23)
<223> OTHER INFORMATION: n=g, a, u, or c

<400> SEQUENCE: 4
nnnnnccucc agaucuagnn nnn                                              23

<210> SEQ ID NO 5
<211> LENGTH: 13
<212> TYPE: RNA
<213> ORGANISM: Artificial Sequence
<220> FEATURE:
<223> OTHER INFORMATION: Chemically synthesized fragment 2;
      psoralentated RNA fragment
<220> FEATURE:
<221> NAME/KEY: modified_base
<222> LOCATION: (6)...(6)
<223> OTHER INFORMATION: n=p
<220> FEATURE:
<221> NAME/KEY: misc_feature
<222> LOCATION: (13)...(13)
<223> OTHER INFORMATION: psoralen bound to G

<400> SEQUENCE: 5
cuagancugg agg                                                         13

<210> SEQ ID NO 6
<211> LENGTH: 30
<212> TYPE: DNA
<213> ORGANISM: Artificial Sequence
<220> FEATURE:
<223> OTHER INFORMATION: chemically synthesized fragment 3; modified
      tRNA; thymine at residue 8 before pseudouridine
<220> FEATURE:
<221> NAME/KEY: modified_base
<222> LOCATION: (9)...(9)
<223> OTHER INFORMATION: n=p
<220> FEATURE:
<221> NAME/KEY: misc_feature
<222> LOCATION: (30)...(30)
<223> OTHER INFORMATION: n=puromycin

<400> SEQUENCE: 6
uccugugtnc gauccacaga auucgcaccn                                       30

<210> SEQ ID NO 7
<211> LENGTH: 43
<212> TYPE: DNA
<213> ORGANISM: Artificial Sequence
<220> FEATURE:
<223> OTHER INFORMATION: Chemically synthesized fragment 2+3; modified
      tRNA; thymine at residue 21 before pseudouridine
<220> FEATURE:
<221> NAME/KEY: modified_base
<222> LOCATION: (22)...(22)
<223> OTHER INFORMATION: n=p
<220> FEATURE:
<221> NAME/KEY: misc_feature
<222> LOCATION: (43)...(43)
<223> OTHER INFORMATION: n=puromycin
<220> FEATURE:
<221> NAME/KEY: modified_base
<222> LOCATION: (6)...(6)
<223> OTHER INFORMATION: n=p

<400> SEQUENCE: 7
cuagancugg agguccugug tncgauccac agaauucgca ccn                        43

<210> SEQ ID NO 8
<211> LENGTH: 33
```

```
<212> TYPE: RNA
<213> ORGANISM: Artificial Sequence
<220> FEATURE:
<223> OTHER INFORMATION: Chemically synthesized fragment 1

<400> SEQUENCE: 8
gcggauuuag cucaguuggg agagcgccag acu                              33

<210> SEQ ID NO 9
<211> LENGTH: 76
<212> TYPE: DNA
<213> ORGANISM: Artificial Sequence
<220> FEATURE:
<223> OTHER INFORMATION: Chemically synthesized fragment 1 + 2 + 3;
      modified tRNA; thymine at residue 54 before
      pseudouridine
<220> FEATURE:
<221> NAME/KEY: modified_base
<222> LOCATION: (39)...(39)
<223> OTHER INFORMATION: n=p
<220> FEATURE:
<221> NAME/KEY: modified_base
<222> LOCATION: (55)...(55)
<223> OTHER INFORMATION: n=p
<220> FEATURE:
<221> NAME/KEY: misc_feature
<222> LOCATION: (76)...(76)
<223> OTHER INFORMATION: n=puromycin
<220> FEATURE:
<221> NAME/KEY: misc_feature
<222> LOCATION: (35)...(36)
<223> OTHER INFORMATION: psoralen binding at UA position

<400> SEQUENCE: 9
gcggauuuag cucaguuggg agagcgccag acucuaganc uggagguccu gugtncgauc    60
cacagaauuc gcaccn                                                    76

<210> SEQ ID NO 10
<211> LENGTH: 32
<212> TYPE: RNA
<213> ORGANISM: Artificial Sequence
<220> FEATURE:
<223> OTHER INFORMATION: chemically synthesized fragment 1; 3' hydroxyl
      at terminus

<400> SEQUENCE: 10
gcggauuuag cucaguuggg agagcgccag ac                                  32

<210> SEQ ID NO 11
<211> LENGTH: 8
<212> TYPE: RNA
<213> ORGANISM: Artificial Sequence
<220> FEATURE:
<223> OTHER INFORMATION: chemically synthesized fragment 2;
      psoralentated RNA
<220> FEATURE:
<221> NAME/KEY: modified_base
<222> LOCATION: (1)...(1)
<223> OTHER INFORMATION: N=p
<220> FEATURE:
<221> NAME/KEY: modified_base
<222> LOCATION: (7)...(7)
<223> OTHER INFORMATION: N=p

<400> SEQUENCE: 11 ncuaacnc                                                              8

<210> SEQ ID NO 12
<211> LENGTH: 36
<212> TYPE: DNA
```

```
<213> ORGANISM: Artificial Sequence
<220> FEATURE:
<223> OTHER INFORMATION: Mixed DNA/RNA chemically synthesized fragment 3
<220> FEATURE:
<221> NAME/KEY: modified_base
<222> LOCATION: (15)...(15)
<223> OTHER INFORMATION: n=p
<220> FEATURE:
<221> NAME/KEY: misc_feature
<222> LOCATION: (36)...(36)
<223> OTHER INFORMATION: n=puromycin

<400> SEQUENCE: 12
uggagguccu gugtncgauc cacagaauuc gcaccn                                   36

<210> SEQ ID NO 13
<211> LENGTH: 18
<212> TYPE: RNA
<213> ORGANISM: Artificial Sequence
<220> FEATURE:
<223> OTHER INFORMATION: chemically synthesized modified RNA fragment
<220> FEATURE:
<221> NAME/KEY: modified_base
<222> LOCATION: (4)...(4)
<223> OTHER INFORMATION: n=p
<220> FEATURE:
<221> NAME/KEY: modified_base
<222> LOCATION: (11)...(12)
<223> OTHER INFORMATION: n=p

<400> SEQUENCE: 13
cccnccagag nnagaccc                                                       18

<210> SEQ ID NO 14
<211> LENGTH: 14
<212> TYPE: RNA
<213> ORGANISM: Artificial Sequence
<220> FEATURE:
<223> OTHER INFORMATION: chemically synthesized fragment 2
<220> FEATURE:
<221> NAME/KEY: modified_base
<222> LOCATION: (7)...(7)
<223> OTHER INFORMATION: n=p
<220> FEATURE:
<221> NAME/KEY: modified_base
<222> LOCATION: (9)...(9)
<223> OTHER INFORMATION: n=p

<400> SEQUENCE: 14
ucuaagncng gagg                                                           14

<210> SEQ ID NO 15
<211> LENGTH: 73
<212> TYPE: DNA
<213> ORGANISM: Artificial Sequence
<220> FEATURE:
<223> OTHER INFORMATION: chemically synthesized; mixed DNA/RNA;
      alternate psoralentated Fragment 1 + 2 + 3
<220> FEATURE:
<221> NAME/KEY: modified_base
<222> LOCATION: (32)...(32)
<223> OTHER INFORMATION: N-3-methyl uridine
<220> FEATURE:
<221> NAME/KEY: misc_feature
<222> LOCATION: (36)...(37)
<223> OTHER INFORMATION: psoralen bound to UA
<220> FEATURE:
<221> NAME/KEY: modified_base
<222> LOCATION: (40)...(40)
<223> OTHER INFORMATION: N=p
<220> FEATURE:
<221> NAME/KEY: modified_base
<222> LOCATION: (42)...(42)
```

<223> OTHER INFORMATION: N=p
<220> FEATURE:
<221> NAME/KEY: misc_feature
<222> LOCATION: (73)...(73)
<223> OTHER INFORMATION: N=puromycin

<400> SEQUENCE: 15
gcggauuuag cucaguuggg agagcgccag anuucuaagn cnggaggucc ugugtycgau    60
ccacagaauu cgn                                                      73

<210> SEQ ID NO 16
<211> LENGTH: 32
<212> TYPE: RNA
<213> ORGANISM: Artificial Sequence
<220> FEATURE:
<223> OTHER INFORMATION: Chemically synthesized fragment 1 ; 3' hydroxyl
      at terminus

<400> SEQUENCE: 16
gcggauuuag cucaguuggg agagcgccag ac                                 32

<210> SEQ ID NO 17
<211> LENGTH: 8
<212> TYPE: RNA
<213> ORGANISM: Artificial Sequence
<220> FEATURE:
<223> OTHER INFORMATION: Chemically synthesized fragment 2 ; 3' hydroxyl
      at terminus
<220> FEATURE:
<221> NAME/KEY: modified_base
<222> LOCATION: (1)...(1)
<223> OTHER INFORMATION: n=p
<220> FEATURE:
<221> NAME/KEY: modified_base
<222> LOCATION: (7)...(7)
<223> OTHER INFORMATION: n=p

<400> SEQUENCE: 17 ncuaaanc                                                             8

<210> SEQ ID NO 18
<211> LENGTH: 36
<212> TYPE: DNA
<213> ORGANISM: Artificial Sequence
<220> FEATURE:
<223> OTHER INFORMATION: Chemically synthesized; mixed DNA/RNA
      fragment 3
<220> FEATURE:
<221> NAME/KEY: modified_base
<222> LOCATION: (15)...(15)
<223> OTHER INFORMATION: N=p
<220> FEATURE:
<221> NAME/KEY: misc_feature
<222> LOCATION: (36)...(36)
<223> OTHER INFORMATION: N=puromycin

<400> SEQUENCE: 18
uggagguccu gugtncgauc cacagaauuc gcaccn                             36

<210> SEQ ID NO 19
<211> LENGTH: 21
<212> TYPE: RNA
<213> ORGANISM: Artificial Sequence
<220> FEATURE:
<223> OTHER INFORMATION: Chemically synthesized; modified RNA fragment
<220> FEATURE:
<221> NAME/KEY: modified_base
<222> LOCATION: (9)...(11)
<223> OTHER INFORMATION: N=p

<400> SEQUENCE: 19 cccccccgann nagaccccccc c                                            21

<210> SEQ ID NO 20
<211> LENGTH: 26
<212> TYPE: RNA
<213> ORGANISM: Artificial Sequence
<220> FEATURE:
<223> OTHER INFORMATION: chemically synthesized; seq A1

<400> SEQUENCE: 20
auauauauau auauauauau gggggg                                         26

<210> SEQ ID NO 21
<211> LENGTH: 26
<212> TYPE: DNA
<213> ORGANISM: Artificial Sequence
<220> FEATURE:
<223> OTHER INFORMATION: Chemically synthesized; seq A2

<400> SEQUENCE: 21 cccccccatat atatatatat atatat                                        26

<210> SEQ ID NO 22
<211> LENGTH: 31
<212> TYPE: RNA
<213> ORGANISM: Artificial Sequence
<220> FEATURE:
<223> OTHER INFORMATION: Chemically synthesized; seq 1B
<220> FEATURE:
<221> NAME/KEY: misc_feature
<222> LOCATION: (1)...(1)
<223> OTHER INFORMATION: no phosphorylation on 5' end

<400> SEQUENCE: 22
gcggauuuag cucaguuggg agagcgccag a                                   31

<210> SEQ ID NO 23
<211> LENGTH: 31
<212> TYPE: RNA
<213> ORGANISM: Artificial Sequence
<220> FEATURE:
<223> OTHER INFORMATION: Chemically synthesized; seq 1B1
<220> FEATURE:
<221> NAME/KEY: misc_feature
<222> LOCATION: (1)...(1)
<223> OTHER INFORMATION: no phosphorylation on 5' end

<400> SEQUENCE: 23
ggggcuuuag cucaguuggg agagcgccag a                                   31

<210> SEQ ID NO 24
<211> LENGTH: 36
<212> TYPE: RNA
<213> ORGANISM: Artificial Sequence
<220> FEATURE:
<223> OTHER INFORMATION: Chemically synthesized RNA sequence
<220> FEATURE:
<221> NAME/KEY: misc_feature
<222> LOCATION: (35)...(36)
<223> OTHER INFORMATION: crosslinker between residue 35 and 36
<220> FEATURE:
<221> NAME/KEY: misc_feature
<222> LOCATION: (36)...(36)
<223> OTHER INFORMATION: phosphorylated

<400> SEQUENCE: 24
gcggauuuag cucaguuggg agagcgccag acucua                              36

-continued

```
<210> SEQ ID NO 25
<211> LENGTH: 36
<212> TYPE: RNA
<213> ORGANISM: Artificial Sequence
<220> FEATURE:
<223> OTHER INFORMATION: Chemically synthesized RNA sequence
<220> FEATURE:
<221> NAME/KEY: misc_feature
<222> LOCATION: (1)...(1)
<223> OTHER INFORMATION: hydroxylated
<220> FEATURE:
<221> NAME/KEY: misc_feature
<222> LOCATION: (35)...(36)
<223> OTHER INFORMATION: crosslinker between residues 35 and 36
<220> FEATURE:
<221> NAME/KEY: misc_feature
<222> LOCATION: (36)...(36)
<223> OTHER INFORMATION: phosphorylated

<400> SEQUENCE: 25
ggggcuuuag cucaguuggg agagcgccag acucua                                    36

<210> SEQ ID NO 26
<211> LENGTH: 61
<212> TYPE: RNA
<213> ORGANISM: Artificial Sequence
<220> FEATURE:
<223> OTHER INFORMATION: Chemically synthesized RNA sequence
<220> FEATURE:
<221> NAME/KEY: misc_feature
<222> LOCATION: (59)...(60)
<223> OTHER INFORMATION: crosslinker between residues 59 and 60

<400> SEQUENCE: 26
ggguuaacuu uagaaggagg ucgccaccau gguuaaaaug aaaaugaaaa ugaaaaugua          60
g                                                                          61

<210> SEQ ID NO 27
<211> LENGTH: 55
<212> TYPE: RNA
<213> ORGANISM: Artificial Sequence
<220> FEATURE:
<223> OTHER INFORMATION: Chemically synthesized RNA sequence M1

<400> SEQUENCE: 27
ggguuaacuu uagaaggagg ucgccaccau gguuaaaaug aaaaugaaaa ugaaa              55

<210> SEQ ID NO 28
<211> LENGTH: 61
<212> TYPE: RNA
<213> ORGANISM: Artificial Sequence
<220> FEATURE:
<223> OTHER INFORMATION: Chemically synthesized RNA sequence
<220> FEATURE:
<221> NAME/KEY: misc_feature
<222> LOCATION: (59)...(60)
<223> OTHER INFORMATION: crosslink between residue 59 and 60
<220> FEATURE:
<221> NAME/KEY: misc_feature
<222> LOCATION: (61)...(61)
<223> OTHER INFORMATION: g bound to biotin
<220> FEATURE:
<221> NAME/KEY: misc_feature
<222> LOCATION: (33)...(34)
<223> OTHER INFORMATION: n=g, a, u, or c

<400> SEQUENCE: 28
ggguuaacuu uagaaggagg ucgccaccau ggnnaaaaug aaaaugaaaa ugaaaaugua          60
``` g                                                              61

<210> SEQ ID NO 29
<211> LENGTH: 61
<212> TYPE: RNA
<213> ORGANISM: Artificial Sequence
<220> FEATURE:
<223> OTHER INFORMATION: Chemically synthesized RNA sequence

<400> SEQUENCE: 29
ggguuaacuu uagaaggagg ucgccaccau gguuaaaaug aaaaugaaaa ugaaaaugua    60
g                                                              61

<210> SEQ ID NO 30
<211> LENGTH: 21
<212> TYPE: RNA
<213> ORGANISM: Artificial Sequence
<220> FEATURE:
<223> OTHER INFORMATION: Chemically synthesized RNA sequence; generic
      version of SEQ ID NO: 19
<220> FEATURE:
<221> NAME/KEY: misc_feature
<222> LOCATION: (1)...(6)
<223> OTHER INFORMATION: n=g, a, c, or u
<220> FEATURE:
<221> NAME/KEY: modified_base
<222> LOCATION: (9)...(11)
<223> OTHER INFORMATION: n=p
<220> FEATURE:
<221> NAME/KEY: misc_feature
<222> LOCATION: (15)...(21)
<223> OTHER INFORMATION: n=g, a, c,  or u

<400> SEQUENCE: 30
nnnnnngann nagannnnnn n                                           21

<210> SEQ ID NO 31
<211> LENGTH: 36
<212> TYPE: DNA
<213> ORGANISM: Artificial Sequence
<220> FEATURE:
<223> OTHER INFORMATION: Chemically synthesized; mixed DNA/RNA sequence
<220> FEATURE:
<221> NAME/KEY: misc_feature
<222> LOCATION: (1)...(1)
<223> OTHER INFORMATION: phosphorylated
<220> FEATURE:
<221> NAME/KEY: misc_feature
<222> LOCATION: (14)...(14)
<223> OTHER INFORMATION: thymine
<220> FEATURE:
<221> NAME/KEY: modified_base
<222> LOCATION: (15)...(15)
<223> OTHER INFORMATION: n=p
<220> FEATURE:
<221> NAME/KEY: misc_feature
<222> LOCATION: (36)...(36)
<223> OTHER INFORMATION: n=puromycin

<400> SEQUENCE: 31
uggagguccu gugtncgauc cacagaauuc gcaccn                            36

<210> SEQ ID NO 32
<211> LENGTH: 36
<212> TYPE: DNA
<213> ORGANISM: Artificial Sequence
<220> FEATURE:
<223> OTHER INFORMATION: Chemically synthesized; Mixed DNA/ RNA sequence
<220> FEATURE:
<221> NAME/KEY: misc_feature
<222> LOCATION: (1)...(1)

-continued

```
<223> OTHER INFORMATION: phosphorylated
<220> FEATURE:
<221> NAME/KEY: misc_feature
<222> LOCATION: (14)...(14)
<223> OTHER INFORMATION: thymine
<220> FEATURE:
<221> NAME/KEY: modified_base
<222> LOCATION: (15)...(15)
<223> OTHER INFORMATION: n=p
<220> FEATURE:
<221> NAME/KEY: misc_feature
<222> LOCATION: (36)...(36)
<223> OTHER INFORMATION: puromycin attached at 3' end

<400> SEQUENCE: 32
uggagguccu gugtncgauc cacagaaucu ccacca                                    36
```

SYSTEM FOR RAPID IDENTIFICATION AND SELECTION OF NUCLEIC ACIDS AND POLYPEPTIDES, AND METHOD THEREOF

RELATED APPLICATIONS

This application is a continuation-in-part of U.S. Ser. No 09/859,809 filed May 17, 2001, now U.S. Pat. No. 6,962,781, which is a nonprovisional application of U.S. Ser. No. 60/206,016 filed May 19, 2000; this application is also a continuation-in-part of International Application No. PCTUS02/37103 filed Nov. 18, 2002, which designates the United States and was published in English, which is nonprovisional application of U.S. Ser. No. 60/346,965 filed Nov. 16, 2001; and this application is also a nonprovisional application of U.S. Ser. No. 60/529,331 filed Dec. 12, 2003, all hereby incorporated by reference herein.

FIELD OF THE INVENTION

The present invention relates generally to compositions and methods for the identification and selection of nucleic acids and polypeptides.

BACKGROUND OF THE INVENTION

Ligand-receptor interactions are of interest for many reasons, from elucidating basic biological site recognition mechanisms to drug screening and rational drug design. It has been possible for many years to drive in vitro evolution of nucleic acids by selecting molecules out of large populations that preferentially bind to a selected target, then amplifying and mutating them for subsequent re-selection (Tuerk and Gold, Science 249:505 (1990), herein incorporated by reference).

The ability to perform such a selection process with proteins would be extremely useful. This would permit in vitro design and production of proteins that bind specifically to chosen ligands. The use of proteins, as compared to nucleic acids, is particularly advantageous because the twenty diverse amino acid side chains in proteins have far more binding possibilities than the four similar chains in nucleic acid side. Further, many biologically and medically relevant ligands bind proteins.

SUMMARY OF THE INVENTION

Several embodiments of the present invention provide compositions and methods for the efficient and rapid identification and selection of nucleic acids and polypeptides. Certain embodiments are particularly advantageous because the identification, selection, and/or evolution of nucleic acids and proteins according to one embodiment of the invention accommodates access to a large and highly varied population of test molecules, a way to select members of the population that exhibit the desired properties, and the ability to reproduce the selected molecules with mutated variations to obtain another large population for subsequent selection.

Several embodiments of the invention are useful for identifying and selecting genes and proteins used in the prevention and treatment of several diseases. For example, if a nucleic acid sequence linked to a disease is known, several embodiments of this invention can be used to quickly and accurately identify and select the corresponding protein. This protein can be then be mass-produced and used as diagnostic or therapeutic agents. Further, if an protein linked to a disease is known, several embodiments of this invention can permit the rapid identification of the corresponding nucleic acid. The nucleic acid can then be used as a diagnostic or therapeutic agent.

Another advantage of several embodiments of the present invention is the ability to overcome the inability of the proteins to reproduce themselves and the inability to link mRNA encoding a polypeptide with the translated product. Additionally, the generation of large peptide libraries and screening methods have, until recently, required that the process have an in vivo expression step. Examples include yeast two- or three-hybrid, yeast display and phage display methods (Fields and Song, Nature 340:245 (1989); Licitra and Liu, PNAS 93:12817 (1996); Boder and Wittrup, Nat Biotechnol 15:553 (1997); and Scott and Smith, Science 249:386 (1990)). In vivo methods, in some cases, suffer from disadvantages, including a limited library size and cumbersome screening steps. Additionally, undesirable selective pressures can be placed on the generation of variants by cellular constraints of the host. Notwithstanding the foregoing, one of skill in the art will appreciate that one embodiment of the current invention can be used using these in vivo methods.

In vitro methods have been developed more recently, using prokaryotic and eukaryotic in vitro translation systems, such as ribosome display (Mattheakis et al., PNAS 91:9022 (1994); Hanes and Plückthun, PNAS 94:4937 (1997); Jermutus et al., Current Opinion in Biotechnology 9:534 (1998), all herein incorporated by reference). These methods link the protein and its encoding mRNA with the ribosome, and the entire complex is screened against a ligand of choice. Potential disadvantages of this method include the large size of the ribosome, which could interfere with the screening of the attached, and relatively tiny, protein. One of skill in the art will appreciate that one embodiment of the current invention can be used using these in vitro methods.

In 1997, two groups of workers developed an in vitro method of attaching a protein to its coding sequence during translation by using the ribosomal peptidyl transferase with puromycin attached to a linker DNA (Szostak et al., International Patent Publication WO 98/31700; Roberts and Szostak PNAS 94:12297 (1997); Nemoto et al., FEBS Letters 414:405 (1997), all herein incorporated by reference). Once the coding sequence and peptides are linked, the peptides are exposed to a selected ligand. Selection or binding of the peptide by the ligand also selects the attached coding sequence, which can then be reproduced by standard means. Both Roberts and Szostak and Nemoto et al. used the technique of attaching a puromycin molecule to the 3' end of a coding sequence by a DNA linker or other non-translatable chain. Puromycin is a tRNA acceptor stem analog which accepts the nascent peptide chain under the action of the ribosomal peptidyl transferase and binds it stably and irreversibly, thereby halting translation.

Several embodiments of the current invention are particularly advantageous because they overcome one or more of the following limitations: (1) the coding sequence encoding each peptide must be known and be modified both initially and between each selection; (2) selection of native unknown mRNAs only; (3) the modification of the coding sequence adds several steps to the process; and (4) the attached puromycin on the linker molecules may compete in the translation reaction with the native tRNAs for the A site on the ribosome reading its coding sequence or a nearby ribosome, and could thus "poison" the translation process, just as would unattached puromycin in the translation reaction solution. Inadvertent interactions between puromycin and ribosomes could result in two kinds of reaction non-specificity: prematurely shortened proteins and proteins attached to the wrong message. There are reports in the prior art that indicate that the avidity of the A site and the peptidyl transferase for the puromycin may be modulated by $Mg^{++}$ concentration (Roberts, Curr. Opin. Chem. Biol. 3:268 (1999), herein incorporated by reference). Although $Mg^{++}$ concentration may be titrated to control for the first kind of non-specificity (e.g., premature termination of translation), it will not affect the second type (e.g., inaccurate mRNA-protein linkage).

Other advantages of some embodiments of the present invention include the ability to generate high yield of crosslinks, the ability to use a full complement of amino acids and the ability to use stop codons.

Thus, a need exists for an in vitro nucleic acid-based protein evolution system that, in some embodiments, does not necessarily require initial knowledge of the nucleic acid's sequence or repeated chemical modification of the nucleic acids, and which can accurately link a mRNA to its protein. There also remains a need for a system that is capable of using the full complement of amino acids with good efficiency in the presence of stop codons.

Several embodiments of the present invention provide compositions and methods to identify, select and evolve desired properties of proteins and nucleic acids. In many embodiments, the current invention provides tRNA molecules, which include modified tRNAs and tRNA analogs. In other embodiments, tRNA molecules include native or unmodified tRNAs. Other embodiments include methods for generating polypeptides, assays enabling selection of individual members of a population of polypeptides having desired characteristics, methods for amplifying the nucleic acids encoding such selected polypeptides, and methods for generating new variants to screen for enhanced properties.

In several embodiments, the present invention permits the attachment of a protein to its respective mRNA without requiring modification of native mRNA. In another embodiment, only minimal modification is needed. In yet another embodiment, extensively modified mRNA can be used. The specificity of the methods embodied in some embodiments are determined by the specificity of the codon-anticodon interaction.

In a preferred embodiment, the invention permits the selection of nucleic acids by selecting the proteins for which they code. This, in one embodiment, this is accomplished by connecting the protein to its cognate mRNA at the end of translation, which in turn is done by connecting both the protein and mRNA to a tRNA molecule.

In one embodiment, a method for identifying a desired protein or nucleic acid molecule is provided. In one embodiment, at least two mRNA molecules are provided. At least one of the mRNA molecules comprises a stop codon and/or a pseudo stop codon. The mRNA molecules is translated to generate at least one translated protein. The mRNA molecules is linked, coupled or associated to its corresponding translated protein using a tRNA molecule to form at least one cognate pair. At least one of the mRNA molecules is connected to the tRNA molecule by a crosslinker. In one embodiment, the cognate pairs is identified using a property of the translated protein or the mRNA molecule. An mRNA molecule of the selected cognate pair, a nucleic acid molecule complementary to the mRNA molecule and/or a nucleic acid molecule homologous to the mRNA molecule is identified, thereby identifying the desired protein or the desired nucleic acid molecule.

In one embodiment, the tRNA molecule is a stable aminoacyl tRNA analog (SATA). As used herein, a SATA is an entity which can recognize a selected codon such that it can accept a peptide chain by the action of the ribosomal peptidyl transferase, preferably when the cognate codon is in the reading position of the ribosome.

In one embodiment, the SATA comprises a puromycin and a crosslinker that are both located on the SATA. The term "located on" as used herein shall be given its ordinary meaning and shall also meaning positioned on, incorporated in, attached to, coupled to, bound to, or integral to. In one embodiment, the SATA comprises a puromycin, but the crosslinker is located on the mRNA molecule. In one embodiment, the crosslinker is located only on the mRNA and not on the tRNA.

In one embodiment, the tRNA molecule is a Linking tRNA Analog. In one embodiment, a crosslinker is located on the Linking tRNA Analog, and no puromycin is present.

In one embodiment, the tRNA molecule is a Nonsense Suppressor tRNA. In one embodiment, a crosslinker is located not on the tRNA, but on the mRNA, and no puromycin is present. In one embodiment, the crosslinker is located only on the mRNA and not on the tRNA. In one embodiment, the Nonsense Suppressor tRNA is a substantially unmodified native tRNA.

In one embodiment of the invention, the crosslinker is an agent that chemically or mechanically links two molecules together. In one embodiment, the crosslinker is an agent that can be activated to form one or more covalent bonds with tRNA and/or mRNA. In one embodiment, the crosslinker is a sulfur-substituted nucleotide. In another embodiment, the crosslinker is a halogen-substituted nucleotide. Examples of crosslinkers include, but are not limited to, 2-thiocytosine, 2-thiouridine, 4-thiouridine, 5-iodocytosine, 5-iodouridine, 5-bromouridine and 2-chloroadenosine, aryl azides, and modifications or analogues thereof. In one embodiment, the crosslinker is psoralen or a psoralen analog. One or more crosslinkers can be used, and the locations of these crosslinkers can be varied.

In one embodiment, the crosslinker is located on the mRNA. In another embodiment, the crosslinker is located on the tRNA molecule. In one embodiment, the crosslinker is located on or near a codon. In another embodiment, the crosslinker is located on or near a stop or pseudo stop codon. In one embodiment, the crosslinker is located on or near an anticodon of the RNA molecule. In one embodiment, the crosslinker is located on or near a stop or pseudo stop anticodon of the RNA molecule.

In one embodiment of the invention, the crosslinker forms a bond or coupling between the tRNA molecule and the mRNA molecule. In one embodiment, the tRNA molecule is connected to its translated protein by ribosomal peptidyl transferase. In another embodiment, the tRNA molecule is connected to the mRNA through an ultraviolet-induced crosslink between the anticodon of the tRNA molecule and the codon of the mRNA.

In one embodiment, the tRNA molecule has a stable peptide acceptor. The stable peptide acceptor, in one embodiment, is a puromycin or puromycin analog. In one embodiment, the tRNA molecule is operable to accept a peptide chain and hold the chain in a stable manner such that ribosomal peptidyl transferase cannot detach it. In one embodiment, the tRNA molecule comprises a moiety which binds to the ribosome, accepts the peptide chain, and then does not act as a donor in the next transpeptidation. The moiety can be located on the tRNA. In one embodiment, the moiety includes, but is not limited to, a 2' ester on a 3' deoxy adenosine, an amino acyl tRNAox-red and a puromycin. One or more moieties may be located on the tRNA molecule.

In one embodiment, the mRNA molecule is untranslatable beyond a linking codon. In one embodiment, the tRNA molecule accepts a peptide chain and holds the chain in a manner such that ribosomal peptidyl transferase cannot detach it because the message in subsequent codons is untranslatable. In another embodiment, the tRNA molecule accepts a peptide chain and holds the chain in a manner such that ribosomal peptidyl transferase cannot detach it because the message is untranslatable. The message can be untranslatable because it is at the end of the message or because the tRNAs that recognize the appropriate codons have been depleted. Other techniques to make the mRNA untranslatable can also be used.

In one embodiment of the current invention, translation is performed in vitro. In another embodiment, translation is performed in situ. In yet another embodiment, in vivo translation is provided.

In another embodiment of the invention, the method further comprises selecting a desired nucleic acid or protein by providing a plurality of cognate pairs, binding at least one of these cognate pairs with one or more binding agents, and selecting the desired protein or nucleic acid molecule based upon a reaction to the binding agents. Section can also be performed based on a lack of reaction to a binding agent.

In one embodiment, the step of providing a plurality of cognate pairs comprises providing one or more cognate pairs on or in a medium selected from the group consisted from one or more of the following: a matrix, in solution, on beads, and on an array. One skilled in the art will understand that cognate pairs can be placed in any medium suitable for further binding or selection. In one embodiment, the cognate pair is selected based upon ligand binding. Ligands include, but are not limited to, proteins, nucleic acids, chemical compounds, polymers and metals. In another embodiment, the reaction is selected from the group consisting of one or more of the following: ligand binding, immunoprecipitation, and enzymatic reactions. One skilled in the art will understand that any reaction that serves to distinguish the target molecule can be used. These reactions include, but are not limited to, chemical, mechanical, and biological reactions.

In another embodiment of the invention, the method further comprises selecting a desired nucleic acid molecule. In one embodiment, the method comprises providing an array of nucleic acids, wherein the nucleic acids are placed in a predetermined position, hybridizing at least one of the cognate pairs onto the array, reacting the cognate pairs with one or more binding agents, and selecting the desired nucleic acid molecule based upon a reaction or lack of a reaction to the binding agent. Binding agents include, but are not limited to ligands, described above. One skilled in the art will understand that any reaction that serves to distinguish the desired nucleic acid molecule can be used. These reactions include, but are not limited to, chemical, mechanical, and biological reactions.

In yet another embodiment, the method further comprises determining the DNA sequence of the translated protein. In one embodiment, the method comprises providing an array of two or more DNA sequences, wherein the DNA sequences are placed in a predetermined position, exposing the array to one or more cognate pairs, wherein one or more cognate pairs comprises an mRNA portion and a protein portion, hybridizing the mRNA portion of the cognate pairs onto the array, exposing the protein portion of one or more cognate pairs to a binding agent, thereby producing a reaction or a non-reaction, and selecting the desired protein based upon the reaction or non-reaction to the binding agent, such as a ligand, thereby determining the DNA sequence of the translated protein.

In one embodiment of the present invention, a modified mRNA molecule operable to crosslink to a tRNA molecule is provided. In one embodiment, the modified mRNA molecule comprises a crosslinker located on or near a stop codon. In one embodiment, the modified mRNA molecule comprises a crosslinker located on or near a pseudo stop codon.

In one embodiment, the crosslinker is an agent that can be activated to form one or more covalent bonds with the tRNA. In one embodiment, the crosslinker is an agent that is activated to form one or more covalent bonds with the tRNA using light. In another embodiment, the crosslinker is a modified base that is incorporated directly into the mRNA. In one embodiment, crosslinker is selected from the group consisting of one or more of the following 2-thiocytosine, 2-thiouridine, 4-thiouridine, 5-iodocytosine, 5-iodouridine, 5-bromouridine and 2-chloroadenosine, aryl azides, and modifications or analogues thereof. In several embodiments, the crosslinker is psoralen.

In one embodiment of the present invention, a kit to generate cognate pairs is provided. In one embodiment, the kit is a compilation, collection, system or group of items that comprise at least one psoralen monoadduct attached to a nonadducted stable aminoacyl tRNA analog. In another embodiment, the kit comprises at least one psoralen monoadduct attached to an oligonucleotide. In several embodiments, the kit comprises instructions regarding the generation of cognate pairs. In yet another embodiments, the kit comprises additional chemicals, agents or equipment that would be useful to generate cognate pairs.

In one embodiment of the invention, a method for evolving desired sequences is provided. In one embodiment, the method comprises: providing at least two candidate mRNA molecules, wherein the mRNA molecule contains a stop codon and/or a pseudo stop codon; translating at least two of the mRNA molecules to generate at least one translated protein, linking at least one of the mRNA molecules to its corresponding translated protein via a tRNA molecule to form at least one cognate pair, wherein at least one of the candidate mRNA molecules is connected to the tRNA molecule by a crosslinker, identifying one or more of the cognate pairs based upon the properties of the translated protein or the mRNA molecule, identifying a molecule selected from the group consisting of one or more of the following: an mRNA molecule of the selected cognate pair, a nucleic acid molecule complementary to the mRNA molecule and a nucleic acid molecule homologous to the mRNA molecule, thereby identifying the desired protein or the desired nucleic acid molecule. The method, in some embodiments, further comprises providing a plurality of cognate pairs, binding at least of the plurality of cognate pairs with one or more binding agents, selecting the desired or protein nucleic acid molecule based upon a reaction or lack of a reaction to the one or more binding agents, thereby selecting a first desired cognate pair. The method, in several embodiments, further comprises recovering the first desired cognate pair to generate a recovered cognate pair, amplifying a first nucleic acid component of the recovered cognate pair, producing a second nucleic acid component, wherein the second nucleic acid component comprises the first nucleic acid component with one or more variations, producing a second protein by translating the second nucleic acid component, linking the second protein with the second nucleic acid component to generate a second desired cognate pair, and obtaining the desired protein sequence by re-selecting the second desired cognate pair based upon at least one desired property.

In one embodiment, the desired property is selected from the group consisting of one or more of the following: binding properties, enzymatic reactions and chemical modifications. In one embodiment, the desired property is a lack of a reaction (or an ability to resist binding, enzymatic reaction or chemical modification). In one embodiment, the step of selecting the first desired cognate pair comprises: providing a first ligand with a desired binding characteristic, contacting one or more of the first cognate pairs with the first ligand to generate unbound complexes and bound complexes, recovering either the bound complexes or the unbound complexes, amplifying at least one nucleic acid component of the recovered complexes, introducing variation to a sequence of the nucleic acid component of the recovered complexes, translating one or more second proteins from the nucleic acid components, linking at least one of the second proteins with at least one of the second nucleic acid components to generate one or more second cognate pairs, and obtaining the desired protein sequence by contacting the at least one of the second cognate pairs with at least one second ligand to select one or more of the second cognate pairs, wherein the second ligand is the same or different than the first ligand.

In one embodiment of the present invention, the invention comprises a method of forming a psoralen monoadduct on a nucleic acid. In one embodiment, the method comprises providing a first nucleic acid and a second nucleic acid, wherein the first nucleic acid and the second nucleic acid are substantially complementary to each other, wherein the first nucleic acid comprises one or more uridine monoadduct targets, and wherein the second nucleic acid comprises at least one pseudouridine. The method further comprises hybridizing at least a portion of the first nucleic acid and the second nucleic acid in the presence of psoralen to form a hybrid, irradiating the hybrid with ultraviolet light, thereby forming the psoralen monoadduct on the first nucleic acid. In one embodiment, one or more uridine monoadduct targets comprises a uridine located adjacent to an adenosine, preferably 3' from the adenosine.

In one embodiment of the invention, a method of producing a psoralen monoadduct or a crosslink is provided. In one embodiment, the method comprises providing a first nucleic acid and a second nucleic acid, wherein the first nucleic acid and the second nucleic acid are substantially complementary to each other, wherein the first nucleic acid comprises one or more uridine monoadduct targets or crosslink targets and one or more uridine monoadduct non-targets or crosslink non-targets, and wherein the uridine monoadduct non-targets or crosslink non-targets are operable to be replaced with one or more pseudouridines. The method further comprises replacing one or more of the uridine monoadduct non-targets or crosslink non-targets with pseudouridine, hybridizing at least a portion of the first nucleic acid and the second nucleic acid in the presence of psoralen to form a hybrid; and irradiating the hybrid, thereby forming the psoralen monoadduct or the crosslink on the first nucleic acid on the targets, while protecting the nontargets. In one embodiment, visible light is used to form the adduct or crosslink. In another embodiment, ultraviolet light is used.

BRIEF DESCRIPTION OF THE DRAWINGS

FIG. 6 illustrates some embodiments of the present invention. The SATA, Linking tRNA Analog and Nonsense Suppressor analog, in certain embodiments, are shown.

DETAILED DESCRIPTION OF THE PREFERRED EMBODIMENT

Various aspects of the present invention use a tRNA mechanism that links messenger RNA (mRNA) to its translated protein product, forming a "cognate pair." In several embodiments, an mRNA, whose sequence is not known, can be expressed, its protein characterized through a selection process against a ligand with desired or selected properties, and nucleic acid evolution—resulting in protein evolution—can be performed in vitro to arrive at molecules with enhanced properties. The cognate pairs are preferably attached via a tRNA molecule.

Figure 3:
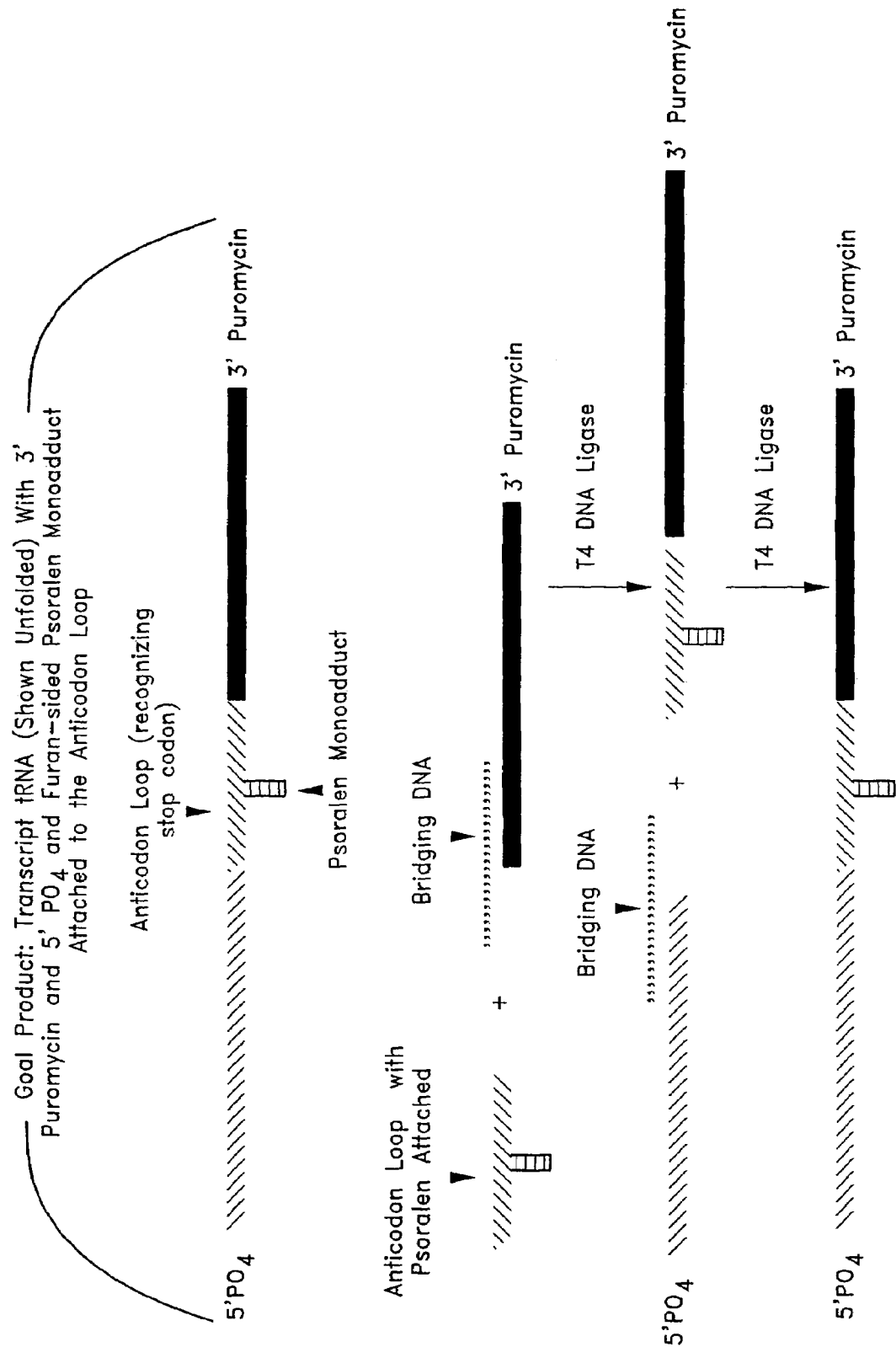
FIG. 3 illustrates one method of construction of a tRNA molecule of the invention. In this embodiment, the 5' end of a tRNA, a nucleic acid encoding an anticodon loop and having a molecule capable of stably linking to mRNA (such as psoralen, as used in this example), and the 3' end of tRNA modified with a terminal puromycin molecule are ligated to form a complete modified tRNA for use in the in vitro evolution methods of the invention. Other embodiments do not include puromycin.

The term "tRNA molecule", as used herein, shall be given it ordinary meaning and shall also mean a stable aminoacyly tRNA analog (SATA), a Linking tRNA Analog, and a Nonsense Suppressor Analog, all of which are described herein. A tRNA molecule includes native tRNA, synthetic tRNA, a combination of native and synthetic tRNA, and any modifications thereof. In a preferred embodiment, the tRNA is connected to the nascent peptide by the ribosomal peptidyl transferase and to the mRNA through an ultraviolet induced crosslink between the anticodon of the tRNA molecule and the codon of the RNA message. This can be done by, for example thiouracil. In one preferred embodiment, the linker is a psoralen crosslink made from a psoralen monoadduct, a non-psoralen crosslinker, or analogs or modifications thereof, pre-placed on either the mRNA's last translatable codon or preferably on the tRNA anticodon of choice. Preferably, a tRNA stop anticodon is selected. A stop codon/anticodon pair selects for full length transcripts. One skilled in the art will understand that an mRNA not having a stop codon may also be used and, further, that any codon or nucleic acid triplet may be used in accordance with several embodiments of the current invention. A tRNA having an anticodon which is not naturally occurring can be synthesized according to methods known in the art (e.g. FIG. 3).

In one embodiment, the anticodon of the tRNA is capable of forming a crosslink to the mRNA, where the cross-link is selected from the group consisting of one or more of the following: 2-thiocytosine, 2-thiouridine, 4-thiouridine 5-iodocytosine, 5-iodouridine, 5-bromouridine and 2-chloroadenosine, aryl azides, and modifications or analogues thereof. These crosslinkers are available commercially from Ambion, Inc. (Austin, Tex.), Dharmacon, Inc. (Lafayette, Colo.), and other well-known manufacturers of scientific materials.

The terms "protein," "peptide," and "polypeptide" are defined herein to mean a polymeric molecule of two or more units comprised of amino acids in any form (e.g., D- or L-amino acids, synthetic or modified amino acids capable of polymerizing via peptide bonds, etc.), and these terms may be used interchangeably herein.

The term "pseudo stop codon" is defined herein to mean a codon which, while not naturally a nonsense codon, prevents a message from being further translated. A pseudo stop codon may be created by using a "stable aminoacyl tRNA analog" or SATA, as described below. In this manner, a pseudo stop codon is a codon which is recognized by and binds to a SATA. Another method by which to create a pseudo stop codon is to create an artificial system in which the necessary tRNA having an anticodon complementary to the pseudocodon is substantially depleted. Accordingly, translation will stop when the absent tRNA is required, e.g., at the pseudo stop codon.

In another embodiment, the selected codon is located on, or placed at, the end of the translatable reading frame by one or more of the following methods (1) having it be the 3' end; (2) providing or having modifications to the moieties 3' to the linking codon, thereby rendering them untranslatable and incapable of activating release factors; and (3) by having codons 3' to the linking codon whose corresponding tRNAs have been depleted.

One skilled in the art will appreciate that are several ways to create a pseudo stop codon that can be used in accordance with several embodiments of the present invention.

The formation of connections between mRNA and its protein product generally requires a tRNA, tRNA analog, or an mRNA with certain characteristics. In several embodiments of the current invention, the tRNA or tRNA analog will have a stable peptide acceptor. This modification changes the tRNA or tRNA analog such that after it accepts the nascent peptide chain by the action of the ribosomal peptidyl transferase, it holds the chain in a stable manner such that the peptidyl transferase cannot detach it. This may be accomplished by using a bond such as a 2' ester on a 3' deoxy adenosine or an amino "acyl tRNA$_{ox\text{-}red}$" which can bind to the ribosome, accept the peptide chain, and then not act as a donor in the next transpeptidation (Chinali et al., Biochem. 13:3001 (1974); Krayevsky and Kukhanova, Prog. Nuc. Acid Res 23:1 (1979) and Sprinzl and Cramer Prog. Nuc. Acid Res 22:1 (1979), all herein incorporated by reference).

In a further embodiment, a selected codon is located on, or placed at, the end of the translatable reading frame by having it be the 3' end or by providing modifications to the more 3' moieties rendering them untranslatable and incapable of recognizing release factors.

In one embodiment, an amino acid or amino acid analog is attached to the 3' end of the tRNA or tRNA analog by a stable bond. This stable bond contrasts the labile, high energy ester bond that connects these two in the native structure. The stable bond not only protects the bond from the action of the peptidyl transferase, but also preserves the structure during subsequent steps. For convenience, this modified tRNA or tRNA analog will be referred to as a "stable aminoacyl tRNA analog" or SATA. As used herein, a SATA is an entity which can recognize a selected codon such that it can accept a peptide chain by the action of the ribosomal peptidyl transferase when the cognate codon is preferably in the reading position of the ribosome. The peptide chain will be bound in such a way that the peptide is bound stably and cannot be unattached by the peptidyl transferase. Preferably, the selected codon is recognized by hydrogen bonding.

One method for creating a stabilized modified tRNA was published in 1973 (Fraser and Rich, PNAS 70:2671 (1973), herein incorporated by reference). This method involves the conversion of a tRNA, or tRNA analog, to a 3'-amino-3'-deoxy tRNA. This is accomplished by adding a 3'-amino-3'-deoxy adenosine to the end of a native tRNA with tRNA nucleotidyl transferase after removing the native adenosine from it with snake venom phosphodiesterase. This modified tRNA is then charged with an amino acid by the respective aminoacyl tRNA synthetase (aaRS). Fraser and Rich used an aaRS in which the tRNA is charged on the 3', rather than the 2', hydroxyl. The amino acid is bound to the tRNA by a stable amide bond rather than the usual labile high-energy ester bond. Thus, when it accepts a peptide from ribosomal peptidyl transferase it will stably hold the peptide and not be able to donate it to another acceptor.

In one embodiment of the present invention, the SATA has a puromycin on the 3' end and a crosslinker (such as psoralen) on the anticodon loop. In another embodiment, the SATA has a puromycin on the 3' end and the crosslinker is located on the mRNA. In some embodiments, where the crosslinker is on the mRNA, the crosslinker is positioned at a stop codon on the mRNA. In other embodiments, the crosslinker is located near a stop codon, preferably between about 1-20 nucleotides away, more preferably 1-10 nucleotides away, and most preferably 1-3 nucleotides away. One skilled in the art will understand that the crosslinker can also be designed to be placed more than 20 nucleotides away from the stop codon. As described herein, psoralen is one example of a crosslinker. Other crosslinkers are described herein.

In yet another embodiment, a Linking tRNA Analog is used to connect the mRNA to its cognate peptide. In one embodiment, the Linking tRNA Analog is a native or a synthetic tRNA (or a combination of native-synthetic hybrid) that has a crosslinker positioned on the anticodon loop. Preferably, the crosslinker is bound to the anticodon loop through covalent bonding. In one embodiment, the Linking tRNA Analog accepts the nascent peptide onto its 3' aminoacyl moiety through the action of ribosomal peptidyl transferase. The 3' aminoacyl moiety can be native to the tRNA or can be synthetically introduced. In one embodiment, the ester bond between the peptide and the tRNA is protected from ribosomal peptidyl transferase because the message is untranslatable beyond the codon bound by the tRNA (the linking codon). Thus, the ribosomal peptidyl transferase will be unable to release the peptide from the tRNA. Therefore, in several embodiments of the present invention, the ester bond between the TRNA and a peptide chain is rugged enough to obviate the need for puromycin. The connection between the Linking tRNA Analog and the peptide, when linked through an ester bond, is protected from dissolution by ribosomal peptidyl transferase by making the translated message "untranslatable" beyond the linking codon. Advantageously, the message then will be stably attached to its peptide for further identification, selection and evolution. Another advantage is that synthetic or modified tRNAs need not be used in some embodiments employing the Linking tRNA Analog. In one particular embodiment, the tRNA is unmodified in the sense that it is unmodified on the 3' end, and may or may not have minor modifications on the anticodon loop. In many embodiments, unmodified native tRNA (particularly unmodified on the 3' end) can be used, therefore making the system, among other things, more cost-effective, efficient, quicker, less error-prone, and capable of producing a much higher yield. Not wishing to bound by the following theory, the inventors believe that absence of puromycin (or similar linkers) results, in some cases, in low yield because puromycin obstruct the interaction of the elongation factor with tRNA thus affecting yield. Further, the elongation factor, when unobstructed by puromycin (or similar linkers) is able to accomplish dynamic proof-reading, thereby reducing error rates.

In a further embodiment, a Nonsense Suppressor tRNA is used. The Nonsense Suppressor tRNA recognizes a stop codon or a pseudo stop codon. The Nonsense Suppressor tRNA is used to connect the mRNA to its cognate peptide. In one embodiment, the Nonsense Suppressor tRNA is a native or a synthetic tRNA (or a combination of native-synthetic hybrid). In one embodiment, the Nonsense Suppressor tRNA has an anticodon triplet that hydrogen bonds to a stop or pseudo stop codon. In one embodiment, the Nonsense Suppressor tRNA has 3' modifications and sequences that conform to the Yarus extended anticodon rules (Yarus, Science 218:646-652, 1982, herein incorporated by reference). In one embodiment, the Nonsense Suppressor tRNA Analog accepts the nascent peptide onto its 3' aminoacyl moiety through the action of ribosomal peptidyl transferase. The 3' aminoacyl moiety can be native to the tRNA or can be synthetically introduced. In one embodiment, the ester bond between the peptide and the tRNA is protected from ribosomal peptidyl transferase because the message is untranslatable beyond the codon bound by the tRNA (the linking codon). Thus, the ribosomal peptidyl transferase will be unable to release the peptide from the tRNA. In a preferred embodiment, the Nonsense Suppressor tRNA does not have any type of crosslinker: the crosslinker is instead located on the mRNA. In some embodiments, where the crosslinker is on the mRNA, the crosslinker is positioned at or near a stop codon on the mRNA. Therefore, several embodiments of the present invention offer several advantages. For example, the surprisingly rugged ester bond between the Nonsense Suppressor tRNA and the means that a puromycin, a puromycin analog, or other amide linker is not needed. Another advantage is that the linkage between the Nonsense Suppressor tRNA and the peptide, when linked through an ester bond, is protected from dissolution by ribosomal peptidyl transferase by making the translated message "untranslatable" beyond the linking codon. Advantageously, the message then will be stably attached to its peptide for further identification, selection and evolution. Thus, in several embodiments, the Nonsense Suppressor tRNA does not need a puromycin nor a crosslinker positioned on the tRNA itself. Yet another advantage is that synthetic or modified tRNAs need no be used. In one particular embodiment, the tRNA is unmodified in the sense that it is unmodified on the 3' end, and may or may not have minor modifications on the anticodon loop. In many embodiments, unmodified native tRNA (particularly unmodified on the 3' end) can be used, therefore making the system, among other things, more cost-effective, efficient, quicker, less error-prone, and able to offer a high yield. Not wishing to be bound by the following theory, the inventors believe that absence of puromycin (or similar linkers) results, in some cases, in low yield because puromycin obstruct the interaction of the elongation factor with tRNA thus affecting yield. Further, the elongation factor, when unobstructed by puromycin (or similar linkers) is able to accomplish dynamic proof-reading, thereby reducing error rates.

A preferred embodiment of the invention comprises a tRNA molecule capable of covalently linking a nucleic acid encoding a polypeptide and the polypeptide to the tRNA. In one embodiment, the linkage of the nucleic acid occurs on a portion of the tRNA other than the linkage to the polypeptide and the tRNA comprises a linking molecule associated with the anticodon of the tRNA. This anticodon of the tRNA is capable of forming a crosslink to the mRNA under irradiation with light of a required wavelength, preferably a furan-sided psoralen monoadduct on the anticodon irradiated with UVA, preferably in the range of about 300-450 nm, more preferably in the range of about 320 to 400 nm, and most preferably about 365 nm. In one embodiment, an amino acid or amino acid analog is attached to the 3' end of a tRNA molecule by a stable bond to generate a SATA. One advantage of some embodiments of the invention is that it ensures that the translation process stalls at this point, thereby making the bond stable in subsequent applications.

In one embodiment, the anticodon of the tRNA is capable of forming a crosslink to the mRNA, where the cross-link is a non-psoralen crosslinker molecule or moiety. As used herein, the term "non-psoralen crosslinker" shall be given its ordinary meaning and shall include one or more of the following compounds: 2-thiocytosine, 2-thiouridine, 4-thiouridine 5-iodocytosine, 5-iodouridine, 5-bromouridine, 2-chloroadenosine, aryl azides, and modifications or analogues thereof.

Other embodiments include an mRNA comprising a psoralen, or a non-psoralen crosslinker, preferably located in the 3' region of the reading frame, more preferably at the most 3' codon of the reading frame, most preferably at the 3' stop codon of the reading frame. In preferred embodiments, the linkage between the tRNA and the mRNA is a cross-linked psoralen, or a non-psoralen crosslinker molecule. In one embodiment, the linkage between the tRNA and the mRNA is a furan-sided psoralen monoadduct.

In several embodiments, the present invention permits the attachment of a protein to its respective mRNA without requiring any or substantial modification of native tRNA. In one embodiment, modified tRNA is used.

One embodiment of the invention comprises an mRNA molecule capable of covalently linking a tRNA that is covalently linked to a polypeptide encoded by the mRNA wherein the tRNA comprises a linking molecule associated with the codon of the mRNA. This codon of the mRNA is capable of forming a crosslink to the tRNA under irradiation with light of a required wavelength. The moiety, which is driven to crosslink, is preferably a furan-sided psoralen monoadduct, or a non-psoralen crosslinker on the codon irradiated with UVA, preferably in the range of about 300-450 nm, more preferably in the range of about 320 to 400 nm, and most preferably about 365 nm. Preferably, this codon is the last (3' most) translatable codon of the reading frame and hence stops translation and is a stop or pseudo stop codon. By making the mRNA untranslatable beyond this point, the use of a bond between the tRNA or tRNA analog and the encoded peptide that is stable to the peptidyl transferase is unnecessary to stall the translation. For many applications, the native ester bond is adequately stable. In one embodiment, the message is made untranslatable by one or more of the following techniques: (1) making the codon the physical end; (2) by using modified nucleotides; (3) by using moieties that can not be processed by the ribosome; and (4) by depleting the tRNAs recognizing the message beyond the selected codon. One of skill in the art will understand that other methods that render the message untranslatable can also be used in accordance with several embodiments of the invention.

One skilled in the art will understand that, in accordance with some embodiments of the present invention, other methods to crosslink an mRNA to a translating tRNA while still in the ribosome can also be used. These methods include, but are not limited to, the use of modified nucleotides such as aryl azides on uracils and guanine residues which provide efficient mRNA-tRNA photo crosslinks in ribosomes (Demeshkina, N, et al., RNA 6:1727-1736, 2000, herein incorporated by reference).

A further embodiment of the invention provides a method of forming a monoadduct. According to one embodiment, a target oligonucleotide with at least one uridine and at least one modified uridine is contacted with psoralen, and the target oligonucleotide and psoralen are coupled to form a monoadduct. The modified uridine according to this embodiment may be modified to avoid coupling with psoralen. In one embodiment, the modified uridine is pseudouridine. According to this embodiment, the target oligonucleotide may be a tRNA molecule, such as tRNA, modified tRNA and tRNA analogs or a mRNA molecule, such as mRNA, modified mRNA and mRNA analogs. In a further embodiment the psoralen is coupled to the target oligonucleotide by one or more cross-links. According to this embodiment, a second oligonucleotide with a nucleotide sequence complementary to the target oligonucleotide sequence may be present. This second oligonucleotide may contain no uridine or may contain uridine residues that are modified to avoid cross-linking with the target oligonucleotide. Preferably, the modified uridine is pseudouridine.

In one embodiment of the present invention, the invention comprises a method of forming a psoralen monoadduct on a nucleic acid. The method, in some embodiments, comprises providing a first nucleic acid and a second nucleic acid that are at least substantially complementary to each other. The first nucleic acid comprises one or more uridine monoadduct targets, and the second nucleic acid comprises at least one pseudouridine. The method further comprises hybridizing at least a portion of the first nucleic acid and the second nucleic acid in the presence of psoralen, or psoralen-like agent, to form a hybrid, irradiating the hybrid with ultraviolet light, thereby forming the psoralen monoadduct on the first nucleic acid. In one embodiment, one or more uridine monoadduct targets comprises a uridine located adjacent to an adenosine, preferably 3' from the adenosine.

In another embodiment, a method of producing a psoralen monoadduct or a crosslink comprises providing a first nucleic acid and a second nucleic acid that are at least substantially complementary to each other. The first nucleic acid comprises one or more uridine monoadduct targets or crosslink targets and one or more uridine monoadduct non-targets or crosslink non-targets. The uridine monoadduct non-targets or crosslink non-targets are operable to be replaced or substituted with one or more pseudouridines. The method further comprises replacing one or more of the uridine monoadduct non-targets or crosslink non-targets with pseudouridine, hybridizing at least a portion of the first and second nucleic acids in the presence of psoralen, forming at least a partial hybrid; and irradiating, or otherwise activating, the hybrid, thereby forming the psoralen monoadduct or the crosslink on the first nucleic acid on the targets, while protecting the nontargets. In one embodiment, visible light is used to form the adduct or crosslink. In another embodiment, ultraviolet light is used.

Several embodiments of the present invention include a method of stably linking a nucleic acid, a tRNA, and a polypeptide encoded by the nucleic acid together to form a linked nucleotide-polypeptide complex. In a preferred embodiment, the nucleic acid is an mRNA and the linked nucleotide-polypeptide complex is a mRNA-polypeptide complex. The method can further comprise providing a plurality of distinct nucleic acid-polypeptide complexes, on, for example, an array, providing a ligand with a desired binding characteristic, contacting the complexes with the ligand, removing unbound complexes, and recovering complexes bound to the ligand.

Several methods of the current invention involve the identification, selection and/or evolution of nucleic acid molecules and/or proteins. In one embodiment, this invention comprises amplifying the nucleic acid component of the recovered complexes and introducing variation to the sequence of the nucleic acids. In other embodiments, the method further comprises translating polypeptides from the amplified and varied nucleic acids, linking them together using tRNA, and contacting them with the ligand to select another new population of bound complexes. Several embodiments of the present invention use selected protein-mRNA complexes in a process of in vitro evolution, in particular the iterative process in which the selected mRNA is reproduced with variation, translated and again connected to cognate protein for selection.

In one embodiment of the current invention, the selected codon is located on, or placed at, the end of the translatable reading frame by having it be the 3' end or having modifications to the more 3' moieties rendering them untranslatable and incapable of recognizing release factors. One advantage of this embodiment is that the amide bonded amino acid analog on the 3' end of the tRNA is not needed to stall translation. Further, this permits efficient production of peptide tRNA complexes. These complexes are quite robust in spite of the high energy content of their ester bond (FIG. 6).

In a preferred method, the SATA or peptidyl-tRNA will be attached to the translated message by a psoralen, or one of the group 2-thio cytosine, 2-thio uridine, 4thio uridine 5-iodocytosine, 5-iodouridine, 5-bromouridine, 2-chloroadenosine, or aryl azides cross link between the codon and anticodon. Psoralen cross links are, in some embodiments, preferentially made between sequences that contain complementary 5' pyrimidine-purine 3' sequences, especially UA or TA sequences (Cimino et al., Ann. Rev. Biochem. 54:1151 (1985), herein incorporated by reference). In some embodiments, non-psoralen crosslinkers or aryl azides are used and in certain embodiments, are particularly advantageous because they are less stringent in their requirements and therefore increase the possible codon-anticodon pairs.

The codon coding for the SATA or the Linking tRNA Analog may be referred to as the linking codon. For the use of psoralen as the crosslinking moiety, the linking codon can be PYR-PUR-X or X-PYR-PUR, so that several codons may be used for the linking codon. "X" in this case, may be any nucleotide. Conveniently, the stop or nonsense codons have this configuration. Using a codon that codes for an amino acid may require minor adjustments to the genetic code, which could complicate some applications. Therefore, in a preferred embodiment, a stop codon is used as the linking codon and the SATA or linking tRNA functions as a nonsense suppressor in that it recognizes the linking codon. One skilled in the art, however, will appreciate that, with appropriate adjustments to the system, any codon can be used.

Fraser and Rich did their work in *E. coli*, but the most effective in vitro translation systems are in eukaryotes The use of prokaryotic suppressors in eukaryotic translation systems appears to be feasible (Geller and Rich Nature 283:41 (1980); Edwards et al PNAS 88:1153 (1991); Hou and Schimmel Biochem 28:6800 (1989), all herein incorporated by reference). They are primarily limited by the resident aaRS's. This limitation is overcome by various embodiments of the present invention because the tRNA or analog can be charged in the prokaryotic system and then purified according to established methods (Lucas-Lenard and Haenni, PNAS 63:93 (1969), herein incorporated by reference).

In several embodiments of the current invention, acceptor stem modifications suitable for use in the tRNAs and analogs can be produced by various methods known in the art. Such methods are found in, for example, Sprinzl and Cramer, Prog. Nuc. Acid Res. 22:1 (1979), herein incorporated by reference. In an alternative embodiment, "transcriptional tRNA", e.g., the sequence of the tRNA as it would be transcribed rather than after the post-transcriptional processing, leads to the atypical and modified bases that are common in tRNAs. These transcriptional tRNAs are capable of functioning as tRNAs (Dabrowski et al., EMBO J. 14: 4872, 1995; and Harrington et al., Biochem. 32: 7617, 1993, both herein incorporated by reference). Transcriptional tRNA can be produced by transcription or can be made by connecting commercial RNA sequences together, piece-wise as in FIG. 3, or in some combination of established methods. For instance, the 5' phosphate and 3' puromycin are commercially available attached to oligoribonucleotides. Commercial RNA sequences are available from Dharmacon Research Inc., La Fayette, Colo. This company can also provide modified native tRNA, such as sequences in which thymine is substituted for uracil and pseudouridine.) These pieces can be connected together using T4 DNA ligase, as is well-known in the art (Moore and Sharp, Science 256: 992, 1992, herein incorporated by reference). Alternatively, in a preferred embodiment, T4 RNA ligase is used (Romaniuk and Uhlenbeck, Methods in Enzymology 100:52 (1983), herein incorporated by reference).

Figure 4:
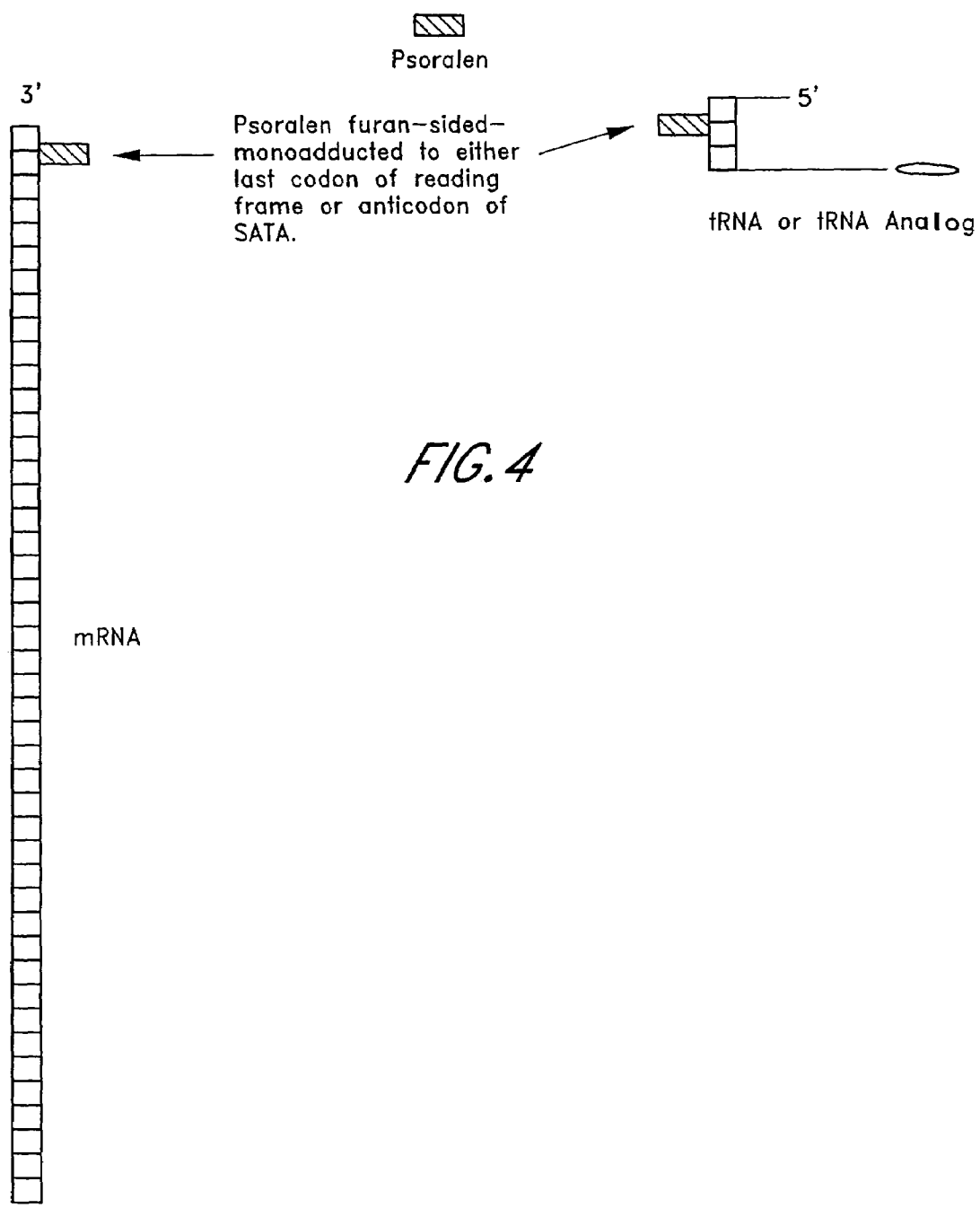
FIG. 4 describes two alternative embodiments by which the crosslinking molecule psoralen can be positioned such that it is capable of linking the mRNA with the tRNA in the methods of the invention. A first embodiment includes linking the crosslinker (e.g., psoralen monoadduct) to the mRNA, and a second embodiment includes linking the crosslinker to the anticodon of the tRNA molecule. The crosslinker can either be monoadducted to the anticodon or the 3' terminal codon of the reading frame for known or partially known messages. This can be done in a separate procedure from translation, e.g., before translation occurs.

In several embodiments of the present invention, psoralen is monoadducted to the SATA or Linking tRNA Analog by construction of a tRNA from pieces including a psoralen linked oligonucleotide (FIG. 3) or by monoadduction to a native or modified tRNA or analog (FIG. 4). In a preferred embodiment, psoralen is first monoadducted to an oligonucleotide containing part of the anticodon loop as described below and this product is then ligated to the remaining fragments of the SATA or Linking tRNA Analog.

In several embodiments, translation will stop when the nascent protein is attached to the tRNA molecule by the peptidyl transferase or by reaching the end of the reading frame. When a large number of ribosomes are in this position the tRNA molecule or the linking tRNA and the mRNA will be connected with UV light. In a preferred method this will be accomplished by having a psoralen, non-psoralen crosslinker, crosslink formed. Psoralens have a furan side and a pyrone side, and they readily intercalate between complementary base pairs in double stranded DNA, RNA, and DNA-RNA hybrids (Cimino et al., Ann. Rev. Biochem. 54:1151 (1985), herein incorporated by reference). Upon irradiation with UV, preferably in the range of 320 nm to 400 nm, cross linking will take place and leave the staggered pyrimidines covalently bound. By either forming crosslinks and photo reversing them or by using selected wavelengths, it is possible to form monoadducts, described more fully below. These will be either pyrone sided or furan sided monoadducts. Upon further irradiation, the furan sided monoadducts can be covalently crosslinked to complementary base pairs. The pyrone sided monoadducts cannot be further crosslinked. The formation of the furan sided psoralen monoadduct (MAf) is also done according to established methods. In a preferred method, the psoralen is attached to the anticodon of the SATA or Linking tRNA Analog. However, psoralen can also be attached at the end of the reading frame of the message, as depicted in FIG. 4.

Methods for large scale production of purified MAf on oligonucleotides are described in the literature (e.g., Speilmann et al., PNAS 89:4514, 1992, herein incorporated by reference), as are methods that require less resources, but have some non-cross-linkable pyrone sided psoralen monoadduct contamination (e.g., U.S. Pat. No. 4,599,303; Gamper et al., J. Mol. Biol. 197: 349 (1987); Gamper et al., Photochem. Photobiol. 40:29 (1984), both herein incorporated by reference). In several embodiments of the current invention, psoralen labeling is accomplished by using either method. In a preferred embodiment, furan sided monoadducts will be created using visible light, preferably in the range of approximately 400 nm-420 nm, according to the methods described in U.S. Pat. No. 5,462,733 and Gasparro et al., Photochem. Photobiol. 57:1007 (1993), both herein incorporated by reference. In one aspect of this invention, a SATA with a furan sided monoadduct or monoadducted oligonucleotides for placement on the 3' end of mRNAs, along with a monoadducted SATA, or other tRNA molecule, are provided as the basis of a kit.

In one embodiment, the formation and reversal of monoadducts and crosslinks are performed according to the methods of Bachellerie et al. (Nuc Acids Res 9:2207 (1981)), herein incorporated by reference. In a preferred embodiment, efficient production of monoadducts, resulting in high yield of the end-product, is accomplished using the methods of Kobertz and Essigmann, J. A. Chem. Soc. 1997, 119, 5960-5961 and Kobertz and Essigmann, J. Org. Chem. 1997, 62, 2630-2632, both herein incorporated by reference.

Figure 5:
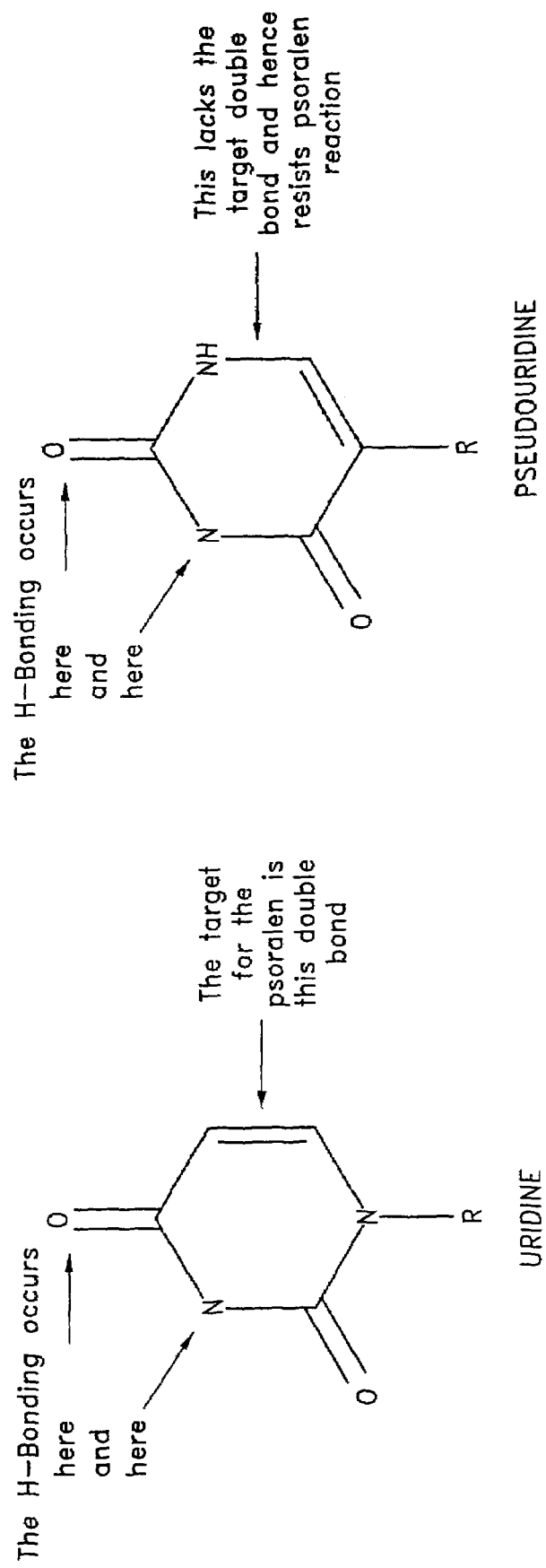
FIG. 5 illustrates the chemical structures for uridine and pseudouridine. Pseudouridine is a naturally occurring base found in tRNA that forms hydrogen bonds just as uridine does, but lacks the 5-6 double bond that is the target for psoralen.

In a preferred embodiment, a tRNA molecule fragment and complementary RNA or DNA is used in which all of the uridines, except the target, are replaced by pseudouridine. FIG. 5 compares the chemical structures for uridine and pseudouridine. Pseudouridine is a naturally occurring base found in tRNA that forms hydrogen bonds just as uridine does. This embodiment is particularly advantageous because the pseudouridine forms the same Watson-Crick hydrogen-bonds as the native uridine but lacks the 5-6 double bond that is the target for interacting with either the furan or pyrone side of the psoralen molecule. This permits the same base-pairing characteristics as an oligonucleotide with uridine, but provides only one target for the psoralen. Because the pyrone side linkage is usually formed after the furan side has reacted, this removal of a staggered target allows the monoadduct to be formed with high efficiency irradiation without forming crosslinks and with minimal formation of pyrone sided monoadduct (MaP). Irradiation is preferably in the range of about 300-450 nm, more preferably in the range of about 320 to 400 nm, and most preferably about 365 nm. More specifically, a pseudouridine on the tRNA molecule permits: 1) the use of tRNA molecule sequences that contain uridines which are potential targets for the psoralen and 2) on the cRNA or cDNA, eliminate the formation of crosslinks, leaving the process stopped at furan sided monoadduct (MaF) formation when using UVA wavelengths which are much more efficient than visible light.

As described herein, non-psoralen crosslinkers, or modifications and analogues thereof, are used in several embodiments. One advantage of non-psoralen crosslinkers is that they are easier to work with in some instances because they can be incorporated into the tRNA or mRNA by commercially available means. For example, use of aryl azide is demonstrated in Demeshkina, N, et al RNA 6:1727-1736, 2000, herein incorporated by reference.

Use of this technology in several embodiments of the current invention is particularly advantageous for in vitro translation systems. However, one skilled in the art will appreciate that in situ systems can also be used. Various embodiments of the current invention will be applicable to any in vitro translation system, including, but not limited to, rabbit reticulocyte lysate (RLL), wheat germ, E. coli, and yeast lysate systems. Many embodiments of the current invention are also well-suited for use in hybrid systems where components of different systems are combined.

tRNAs aminoacylated on a 3' amide bond are reported not to combine with the elongation factor EF-TU which assists in binding to the A site (Sprinzl and Cramer, Prog. Nuc. Acid Res. 22:1 (1979), herein incorporated by reference). Such modified tRNAs do, however, bind to the A site. This binding of 3' modified tRNAs can be increased by changing the $Mg^{++}$ concentration (Chinali et al., Biochem. 13:3001 (1974), herein incorporated by reference). The appropriate concentrations and/or molar ratios of SATA and $Mg^{++}$ can be determined empirically. If the concentration or A site avidity of SATA is too high, the SATA could compete with native tRNAs for non-cognate codons (could function much like puromycin and stall translation). If the concentration or A site avidity of SATA is too low, the SATA might not effectively compete with the release factors, e.g., it would not act as an effective nonsense suppressor tRNA. The balance between these can be determined empirically. Binding of the tRNA to the ribosome A site in the presence of the cognate codon can be enhanced considerably by applying the guidelines for the "extended anticodon" (Yarus, Science 218:646-652, 1982, herein incorporated by reference).

It is also believed that the elongation factor aids in proofreading the codon-anticodon recognition. The error rate in the absence of elongation factor and the associated GTP hydrolysis is estimated to be 1 in 100 for codons one nucleotide away (Voet and Voet, Biochemistry $2^{nd}$ ed. pp. 1000-1002 (1995), John Wiley and Sons, herein incorporated by reference). In a preferred embodiment, UAA is used as the linking codon. For UAA as the linking codon, there are 7 non stop codons which differ by one amino acid. This is 7/61 or about 11.5% of the non stop codons. One can estimate the probability of miscoding a given codon as $(0.01)(0.115)=1.15\times10^{-3}$ miscodes per codon. Thus, one would expect a miscode about every 870 codons, a frequency which will not substantially impair performance in several embodiments of the current invention.

In one embodiment, use of the mRNA with the selected codon at the end of the translatable reading frame would obviate this issue, e.g., by having it be the 3' end or having modifications to the more 3' moieties rendering them untranslatable and incapable of recognizing release factors, or by depleting the tRNAs cognate to any codons 3' of the linking codon. In an alternative embodiment, UAG or UGA is used as the linking codon.

In several embodiments, appropriate concentrations of SATA or linking tRNA and $Mg^{++}$ are used in the in vitro translation system, e.g. RRL, in the presence of the mRNA molecules in the pool, causing translation to cease when the ribosome reaches the codon which permits the SATA to accept the peptide chain or is the last translatable codon that stops the translation at the linking tRNA (the linking codon described above). Within a short time, most of the linking codons will be occupied by SATAs within ribosomes. In a preferred embodiment, the system then will be irradiated with UV light, preferably at approximately 320 nm to 400 nm. Nucleic acids are typically transparent to (do not absorb this wavelength range). Upon irradiation, the psoralen monoadduct will convert to a crosslink connecting the anticodon and the codon by a stable covalent bond.

In a preferred embodiment, the target mRNA is pre-selected. In another embodiment, the target mRNA is artificially produced. In an alternative embodiment, the target consists of messages native to the system under investigation, which may be unknown and/or unidentified. The ability to use unknown and/or unidentified mRNAs is a particular advantage of several embodiments of the current invention.

In several embodiments, once all the nascent proteins are connected to their cognate mRNAs, the ribosomes are released or denatured. Preferably, this is accomplished by the depletion of $Mg^{++}$ through dialysis, simple dilution, or chelation. One skilled in the art will understand that other methods, including, but not limited to, denaturation by changing the ionic strength, the pH, or the solvent system can also be used.

In several embodiments of the invention, the selection of cognate pairs will be based upon affinity binding of proteins according to any of a variety of established methods, including, but not limited to, arrays, affinity columns, immunoprecipitation, and many high throughput screening procedures. A variety of ligands may also be used, including, but not limited to, proteins, nucleic acids, chemical compounds, polymers and metals. In addition, cell membranes or receptors, or even entire cells may be used to bind the cognate pairs. The selection can be positive or negative. That is, the selected cognate pairs can be those that do bind well to a ligand or those that do not. For instance, for a protein to accelerate a thermodynamically favorable reaction, e.g., act as an enzyme for that reaction, it should bind both the substrate and a transition state analog. However, the transition state analog should be bound much more tightly than the substrate. This is described by the equation $$\frac{k_{enzyme}}{k_{\varphi enzyme}} = \frac{K_{trans}}{K_{subst}}$$

where the ratio of the rate of the reaction with the enzyme, $k_{enzyme}$, to the rate without, $k_{\psi enzyme}$, is equal to the ratio of the binding of the transition state to the enzyme $K_{trans}$ over the binding of the substrate to the enzyme Ksubst (Voet and Voet, Biochemistry 2nd ed. p.380, (1995), John Wiley and Sons, herein incorporated by reference).

In a preferred embodiment, proteins which compete poorly for binding to the substrate but compete well for binding to the transition state analog are selected. Operationally, this may be accomplished by taking the proteins that are easily eluted from a matrix with substrate or substrate analog bound to it and are the most difficult to remove from matrix with transition state analog bound to it. By sequentially repeating this selection and reproducing the proteins through replication and translation of the nucleic acid of the cognate pairs, an improved enzyme should evolve. Affinity to one entity and lack of affinity to another in the sane selection process is used in several embodiments of the current invention. Selection can also be done by RNA in many embodiments.

Once the selection has identified a population of cognate pairs it may be convenient to detach the mRNA strand from the tRNA molecule to reproduce it. This is not always necessary, but when desired in certain embodiments, can be accomplished by using psoralen as the connecting photolinker and irradiating the pairs with UV, preferably at approximately 313 nm or just below. This has been identified as a wave length that will photoreverse the psoralen crosslink to MAf and damage the nucleic acid minimally. The ratio of photoreversal to nucleic acid damage is estimated to be 1 photoreversal for damage to 1 in 600 bases (Cimino et al., Biochem 25:3013 (1986), herein incorporated by reference).

One skilled in the art will appreciate that the mRNAs can be reproduced in many ways including, but not limited to, by RNA-dependent RNA polymerases or by reverse transcription and PCR. This can take place using mRNAs separated from the cognate pairs, e.g., using poly T or poly U to hybridize to the poly A tails of, for instance, native unknown messages or by leaving the cognate pairs intact and using oligonucleotide primers that hybridize partially into the reading frame for known messages. Alternatively, commercial kits for rapid amplification of cDNA ends may be used. In several embodiments, the methods described above for placement of photoactivatable moieties on oligonucleotides can be used to create modified oligoribonucleotides which can then be attached to the 3' ends of the message using T4 RNA ligase. The oligonucleotides attached would contain the linking codon with its photoactivatable moiety.

As described herein, there are several ways to connect the message to the tRNA in accordance with several embodiments of the present invention. For example, the following table outlines some embodiments of the current invention:

|  | Stable Acceptor | Native Esterified Acceptor |
|---|---|---|
| Cross-linker on tRNA Analog | tRNA Analog Characteristics:<br>1) Stable acceptor<br>2) Anticodon loop crosslinker<br>3) Recognizes linking codon<br>mRNA Characteristics:<br>1) Flexible; can be a stop or a pseudo stop codon | tRNA Analog Characteristics:<br>1) aaRS for aminoacylating or chemical aminoacylation<br>2) Anticodon loop crosslinker<br>3) Recognizes linking codon<br>mRNACharacteristics:<br>1) Untranslatable beyond linking codon. |
| Cross-linker on mRNA | tRNA Analog Characteristics:<br>1) Stable acceptor<br>2) Recognizes linking codon<br>mRNACharacteristics:<br>1) Crosslinker on or near linking codon | tRNA Analog Characteristics:<br>1) Recognizes linking codon<br>2) Means to aminoacylate (Native nonsense suppressor can work)<br>mRNACharacteristics:<br>1) Contains linking codon<br>2) Untranslatable beyond linking codon<br>3) Crosslinker on or near linking codon |

In one embodiment, at least one amino acid substitution at each position in the protein is sampled. This is particularly advantageous for the evolution of proteins.

The Replication Threshold

A nominal minimum number of replications for efficient evolution may be estimated using the following formulae. If there is a sequence which is n sequences in length, with a selective improvement r mutations away with a mutation rate of p, the probability of generating the selective improvement on replication may be determined as follows:

For r=1, probability of a mutation at the right point, p, times the probability that it mutated to the right one of the three nucleotides that are different from the starting point, ⅓, times the probability that the other n–1 sites remain unmutated, $(1-p)^{(n-r)}$, or $$P_r = \left(\frac{p}{3}\right)^1 (1-p)^{(n-1)}$$

where, P=the probability of attaining a given change r mutations away. More generally, for all r values:

$$P_r = \left(\frac{p}{3}\right)^r (1-p)^{(n-r)}$$

It is instructive to compare the chances of finding an advantage one mutation away with the chances three mutations away. This is because, given the triplet genetic code, any given codon can only change into nine other codons in one mutation. Indeed, it turns out that no codon can actually change into nine other amino acid codes in one mutation. The maximum number of amino acids that can be accessed in one mutation is seven amino acids and there are only eight codons of the sixty-four that can do this. Most codons have five or six out of nineteen other amino acids within one mutation. To reach all nineteen amino acids that are different from the starting one requires, in general, three mutations. These three mutations cannot be sequential since the two intervening ones will not, in general, be selectively advantageous. Therefore we need to use steps that are, at least, three mutations in size (r=3) to use all 20 amino acids.

For a mutation rate of 0.0067, which is that reported for "error-prone PCR", using a message of 300 nucleotides, which gives a short protein of 100 amino acids:

$P_3 = 1.51 \times 10^{-9}$

Therefore, one would expect to need a threshold of:

$$\frac{1}{1.51 \times 10^{-9}} = 6.64 \times 10^8$$

replications at that mutation rate to reasonably expect to reach the next amino acid that is advantageous. This is not the replication to use since the binomial expansion shows that over ⅓ of trials (actually about 1/e) would not contain the given sequence with selective advantage.

A poisson approximation for large n and small p for a given μ can be calculated so that we can compute the general term when n is, say, of the order $10^9$ and p is of the order $10^{-9}$. The general term of the approximation is:

$$\frac{\mu^r}{r! e^\mu}$$

An amplification factor of greater than approximately 6/P ensures that evolution will progress with the use of all amino acids. This is useful when the production of novel proteins precludes the use of "shuffling" of preexisting proteins.

Limits on Purification

Given a reversible binding where B and C compete for A:

$$AB \leftrightarrow A + B \qquad AC \leftrightarrow A + C$$

$$k_B = \frac{[A][B]}{[AB]} \qquad k_C = \frac{[A][C]}{[AC]}$$

$$[B] = k_B \frac{[AB]}{[A]} \qquad (1)$$

$$[C] = k_C \frac{[AC]}{[A]} \qquad (2)$$

The total concentrations can be expressed as follows:

$$[B]_T = [B] + [AB] \qquad (3)$$

$$[C]_T = [C] + [AC] \qquad (4)$$

Dividing (3) by (4):

$$\frac{[B]_T}{[C]_T} = \frac{[B] + [AB]}{[C] + [AC]}$$

And substituting (1) and (2) for [B] and [C]:

$$\frac{[B]_T}{[C]_T} = \frac{k_B \left[\frac{AB}{A}\right] + [AB]}{k_C \left[\frac{AC}{A}\right] + [AC]}$$

Rearranging the equation gives the following results:

$$\frac{[B]_T}{[C]_T} = \frac{[AB]\left(\frac{k_B + [A]}{[A]}\right)}{[AC]\left(\frac{k_C + [A]}{[A]}\right)}$$

Canceling the [A]'s in the numerator and denominator:

$$\frac{[B]_T}{[C]_T} = \frac{[AB](k_B + [A])}{[AC](k_C + [A])}$$

Finally, rearranging the equation provides the following equation:

$$\frac{[AB]}{[AC]} = \frac{[B]_T(k_C + [A])}{[C]_T(k_B + [A])}$$

$$\frac{(k_C + [A])}{(k_B + [A])} \quad \text{(Enrichment Factor)}$$

The above factor is termed the "Enrichment Factor". The ratio of the total components is multiplied by this factor to calculate the ratio of the bound components, or the enrichment of B over C. The maximum enrichment factor is $k_C/k_B$, when the [A] is significantly smaller than $k_C$ or $k_B$. When [A] is significantly greater than $k_C$ or $k_B$, the enrichment is 1, that is, there is no enrichment of one over the other.

The enrichment is limited by the ratio of binding constants. To enrich a scarce protein that is bound 100 times as strongly as its competitors, the ratio of that protein to its competitors is increased by 1 million with 3 enrichments. To enrich a protein that only binds twice as strongly as its competitors, 10 enrichment cycles would gain only an enrichment of ~1000.

By an exactly analogous method an enrichment factor of selecting proteins that bind least well can be shown:

In the equation:

$$\frac{[C]}{[B]} = \frac{k_C[C]_T([A] + k_B)}{k_B[B]_T([A] + k_C)}$$

The enrichment here is maximal at $[A] > k_A$ or $k_B$.

$$\frac{k_C([A] + k_B)}{k_B([A] + k_C)}$$

The following Examples illustrate various embodiments of the present invention and are not intended in any way to limit the invention.

EXAMPLE 1

Production of the SATA Using Uridine

One skilled in the art will understand that the SATA can be produced in a number of different ways. The protocols described below in the following examples can be used for SATAs that have both a puromycin and a crosslinker on the tRNA, or that have a puromycin on the tRNA and a crosslinker on the mRNA. Where the crosslinker is on the mRNA, Example 4, below, provides guidance. The following protocol is also instructive for Linking tRNA Analogs, in the sense that Linking tRNA Analogs also, in a preferred embodiments, have a crosslinker on the tRNA.

Figure 1:
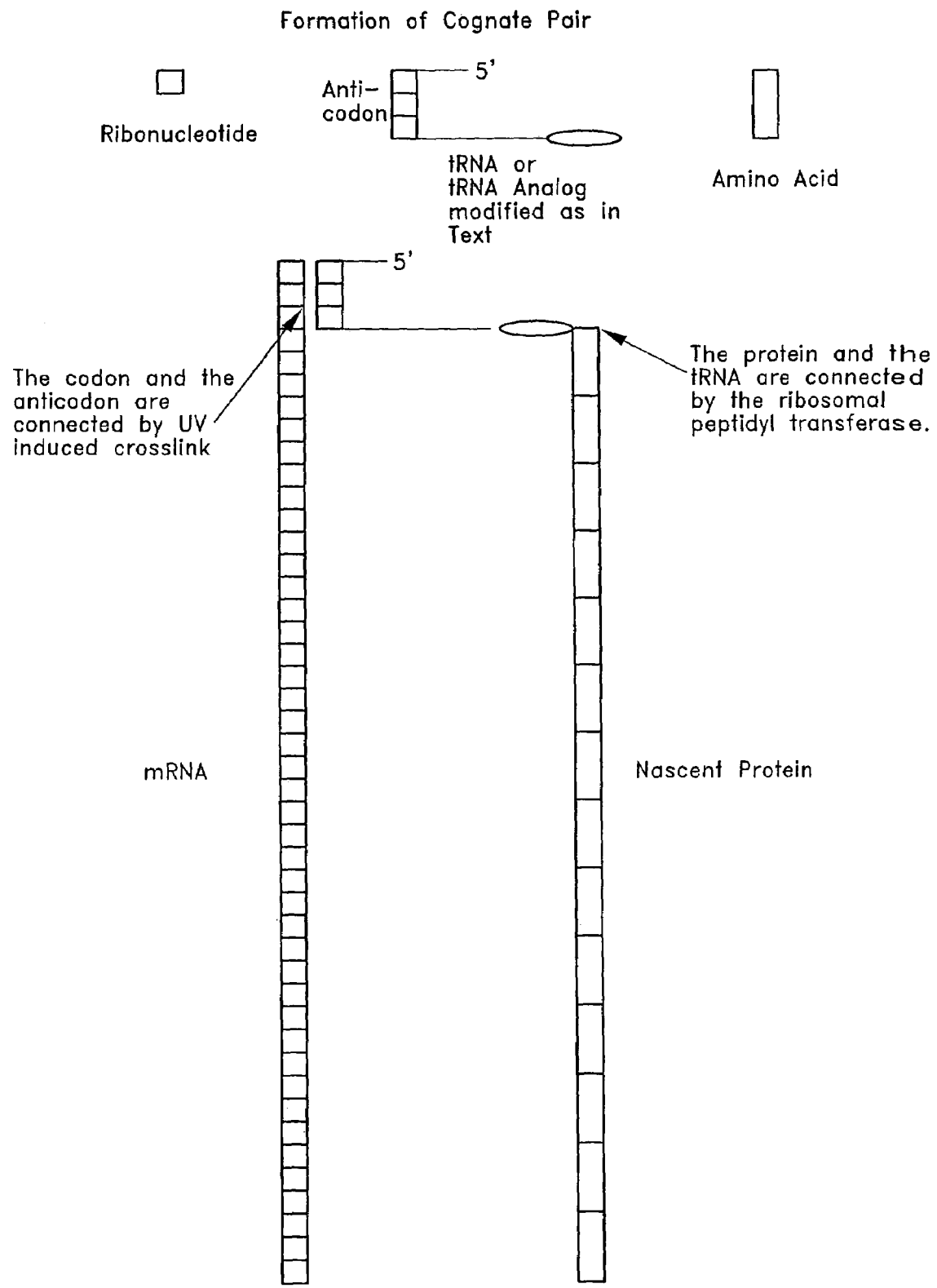
FIG. 1 illustrates schematically one example of the complex formed by the mRNA and its protein product when linked by a modified tRNA or analog. As shown, a codon of the mRNA pairs with the anticodon of a modified tRNA and is covalently crosslinked to a psoralen monoadduct, or a non-psoralen crosslinker or aryl azides by UV irradiation. The translated polypeptide is linked to the modified tRNA via the ribosomal peptidyl transferase. Both linkages occur while the mRNA and nascent protein are held in place by the ribosome.
Figure 2:
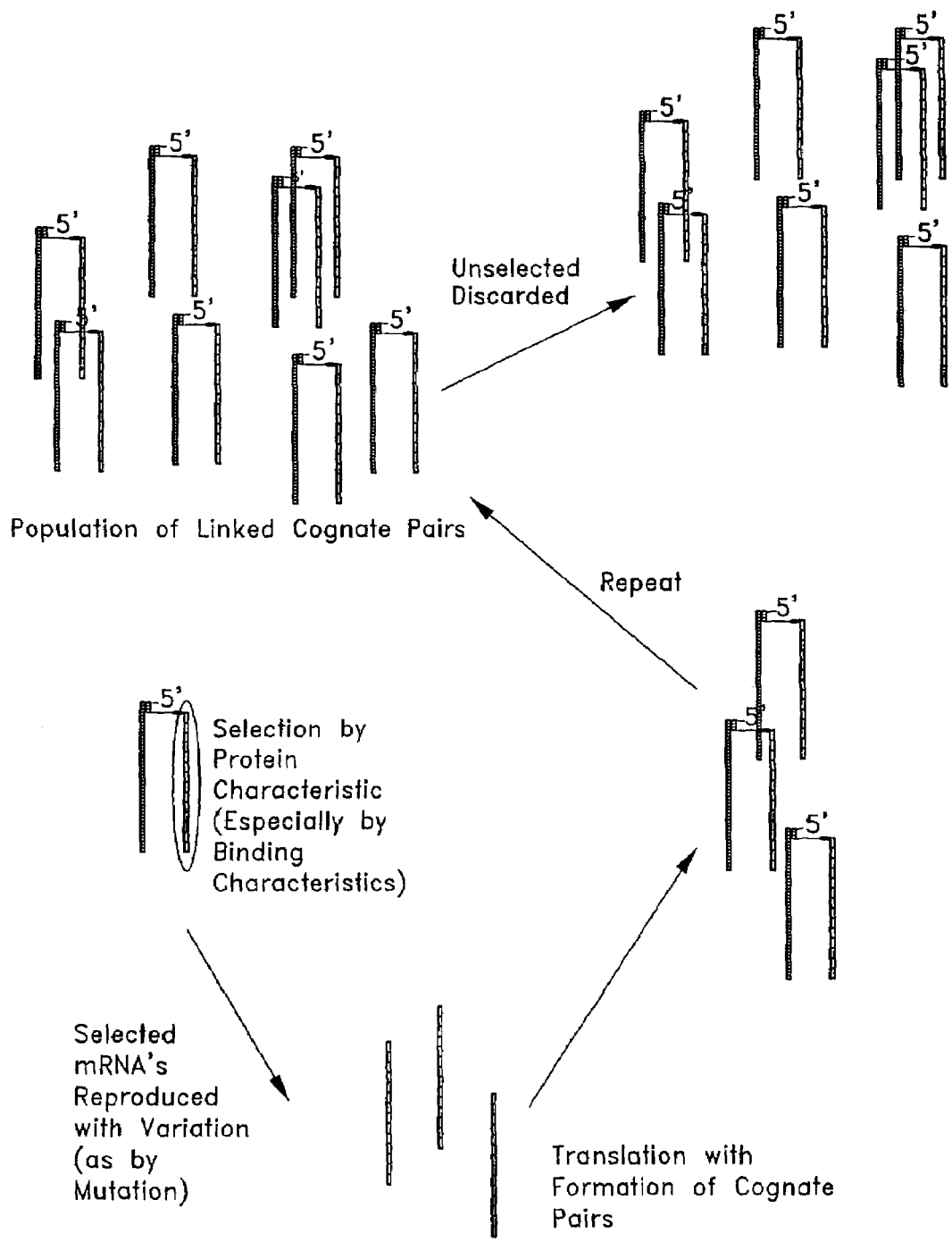
FIG. 2 illustrates schematically an example of the in vitro selection and evolution process, wherein the starting nucleic acids and their protein products are linked (e.g., according to FIG. 1) and are selected by a particular characteristic exhibited by the protein. Proteins not exhibiting the particular characteristic are discarded and those having the characteristic are amplified with variation, preferably via amplification with variation of the mRNA, to form a new population. In various embodiments, nonbinding proteins will be selected. The new population is translated and linked via a modified tRNA or analog, and the selection process is repeated. As many selection and amplification/mutation rounds as desired can be performed to optimize the protein product.

For example, in a preferred embodiment, three fragments (FIG. 1) were purchased from a commercial source (e.g., Dharmacon Research Inc., Boulder, Colo.). Modified bases and a fragment 3 with a pre-attached puromycin on its 3' end and a PO4 on its 3' end were included, all of which were available commercially. Three fragments were used to facilitate manipulation of the fragment 2 in forming the monoadduct.

Yeast tRNAAla or yeast tRNAPhe were used; however, sequences can be chosen from widely known tRNAs or by selecting sequences that will form into a tRNA-like structure. Preferably, sequences with only a limited number of U's in the portion that corresponds to the fragment 2 are used. Using a sequence with only a few U's is not necessary because psoralen preferentially binds 5'UA3' sequences (Thompson J. F., et al Biochemistry 21:1363, herein incorporated by reference). However, there would be less doubly adducted product to purify out if such a sequence was used.

Fragment 2 was preferably used in a helical conformation to induce the psoralen to intercalate. Accordingly, a complementary strand was required. RNA or DNA was used, and a sequence, such as poly C to one or both ends, was added to facilitate separation and removal after monoadduct formation was accomplished.

Fragment 2 and the cRNA were combined in buffered 50 mM NaCl solution. The Tm was measured by hyperchromicity changes. The two molecules were re-annealed and incubated for 1 hour with the selected psoralen at a temperature ~10° C. less than the Tm. The psoralen was selected based upon the sequence used. A relatively insoluble psoralen, such as 8 MOP, could be selected which has a higher sequence stringency but may need to be replenished. A more soluble psoralen, such as AMT, has less stringency but will fill most sites. Preferably, HMT is used. If a fragment 2 is chosen that contains more non-target U's, a greater stringency is desired. Decreasing the temperature or increasing ionic strength by adding Mg++ was also used to increase the stringency. In a preferred embodiment, MG++ was omitted and ~400 mM NaCl solution was used.

Following incubation, psoralen was irradiated at a wavelength greater than approximately 400 nm. The irradiation depends on the wavelength chosen and the psoralen used. For instance, approximately 419 nm 20-150 J/cm2 was preferably used for HMT. This process results in an almost entirely furan sided monoadduct.

Purification of a Monoadduct

The monoadduct was then purified by HPLC as described in Sastry et al, J. Photochem. Photobiol. B Biol. 14:65-79, herein incorporated by reference. The fact that fragment 2 was separate from fragment 3 facilitated the purification step because, generally, purification of monoadducts ≧25 mer is difficult (Spielmann et al. PNAS 89: 4514-4518, herein incorporated by reference).

Ligation of Fragment 2 and 3

The fragment 2 was ligated to the fragment 3 using T4 RNA ligase. The puromycin on the 3' end acted as a protecting group. This is done as per Romaniuk and Uhlenbeck, Methods in Enzymology 100:52-59 (1983), herein incorporated by reference. Joining of fragment 2+3 to the 3' end of fragment 1 was done according to the methods described in Uhlenbeck, Biochemistry 24:2705-2712 (1985), herein incorporated by reference. Fragment 2+3 was 5' phosphorylated by polynucleotide kinase and the two half molecules were annealed.

In an alternative method, significant quantities of furan sided monoadducted U were formed by hybridizing poly UA to itself and irradiating as above. The poly UA was then enzymatically digested to yield furan sided U which was protected and incorporated into a tRNA analog by nucleoside phosphoramidite methods. Other methods of forming the psoralen monoadducts include the methods described in Gamper et al., J. Mol. Biol. 197: 349 (1987); Gamper et al., Photochem. Photobiol. 40:29, 1984; Sastry et al, J. Photochem. Photobiol. B Biol. 14:65-79; Spielmann et al. PNAS 89:4514-4518, U.S. Pat. No. 4,599,303, all herein incorporated by reference.

SATAs generated by the methods described above read UAG (anticodon CUA). Additionally, UAA or UGA was also used. In various embodiments, any message that had the stop codon that was selected as the "linking codon" was used.

Production of Psoralenated Furan Sided Monoadducts

UV Light Exposure Of RNA:DNA Hybrids

Equal volumes of 3 ng/ml RNA:cRNA hybrid segments and of 10 μg/ml HMT both comprised of 50 mM NaCl were transferred into a new 1.5 ml capped polypropylene microcentrifuge tube and incubated at 37° C. for 30 minutes in the dark. This was then transferred onto a new clean culture dish. This was positioned in a photochemical reactor (419 nm peak Southern New England Ultraviolet Co.) at a distance of about 12.5 cm so that irradiance was ~6.5 mW/cm2 and irradiated for 60-120 minutes.

Removal of Low Molecular Weight Protoproducts

100 μl of chloroform-isoamyl alcohol (24:1) was pipetted and mixed by vortex. The mixture was centrifuged for 5 minutes at 15000×g in a microcentrifuge tube. The chloroform-isoamyl alcohol layer was removed with a micropipette. The chloroform-isoamyl alcohol extraction was repeated once again. Clean RNA was precipitated out of the solution.

Alcohol Precipitation

Two volumes (~1000 μl) ice cold absolute ethanol was added to the mixture. The tube was centrifuged for 15 minutes at 15,000×g in a microcentrifuge. The supernatant was decanted and discarded and the precipitated RNA was redissolved in 100 μl DEPC treated water then re-exposed to the RNA+8-MOP.

Isolation of the Psoralenated RNA Fragments Using HPLC

All components, glassware and reagents were prepared so that they were RNAase free. The HPLC was set up with a Dionex DNA PA-100 package column. The psoralenated RNA:DNA hybrid was warmed to 4° C. The psoralenated RNA was applied to HPLC followed by oligonucleotide analysis, as described in the following section entitled "Oligonucleotide Analysis by HPLC." The collected fractions represented:

```
5'CUAGAΨCUGGAGG3', where Ψ is       (SEQ ID NO: 1)
pseudouridine

Furan sided
5'CUPsoralenAGAΨCUGGAGG3'           (SEQ ID NO: 2)
monoadducts

5'XXXXXCCUCCAGAUCUAGXXXXX3'         (SEQ ID NO: 3)

5'XXXXXCCUCCAGAUCUPsoralenAGXXXXX3' (SEQ ID NO: 4)
```

The fractions were stored at 4° C. in new, RNAase free snapped microcentrifuge tubes and stored at −20° C. if more than four weeks of storage were required.

Identification of the RNA Fragments Represented by Each Peak Fraction Collected by HPLC Using Polyacrylamide Gel Electrophoresis (PAGE)

The electrophoresis unit was set up in a 4° C. refrigerator. A gel was selected with a 2 mm spacer. Each 5 μl of HPLC fraction was diluted to 10 μl with Loading Buffer. 10 μl of each diluted fraction was loaded into appropriately labeled sample wells. The tracking dye was loaded in a separate lane and electrophoresis was run as described in the following section entitled "Polyacrylamide Gel Electrophoresis (PAGE) of Psoralenated RNA Fragments." After the electrophoresis run was complete, the electrophoresis was stopped when the tracking dye reached the edge of the gel. The apparatus was disassembled. The gel-glass panel unit was placed on the UV light box. UV lights were turned on. The RNA bands were identified. The bands appeared as denser shadows under UV lighting conditions.

Extraction of the RNA from the Gel

Each band was excised with a new sterile and RNAase free scalpel blade and transferred into a new 1.5 ml snap capped microcentrifuge tube. Each gel was crushed against the walls of the microcentrifuge tubes with the side of the scalpel blade. A new blade was used for each sample. 1.0 ml of 0.3M sodium acetate was added to each tube and eluted for at least 24 hours at 4° C. The eluate was transferred to a new 0.5 ml snap capped polypropylene microcentrifuge tube with a micropipette. A new RNAase free pipette tip was used for each tube and the RNA with ethanol was precipitated out.

Ethanol Precipitation

Two volumes of ice cold ethanol was added to each eluate then centrifuged at 15,000×g for 15 minutes in a microcentrifuge. The supernatants were discharged and the precipitated RNA was re-dissolved in 100 µl of DEPC treated DI water. The RNA was stored in the microcentrifuge tubes at 4° C. until needed. The tubes were stored at −20° C. if storage was for more than two weeks. The following was order of rate of migration for each fragment in order from fastest to slowest:

```
5'CUAGAΨCUGGAGG3'                      (SEQ ID NO: 1)

Furan sided
5'CUPsoralenAGAΨCUGGAGG3'              (SEQ ID NO: 2)
monoadducts

5'XXXXXCCUCCAGAUCUAGXXXXX3'            (SEQ ID NO: 3)

5'XXXXXCCUCCAGAUCUPsoralenAGXXXXX3'    (SEQ ID NO: 4)
```

The tubes containing the remainder of each fraction were labeled and stored at −20° C.

Ethanol Precipitation

RNA oligonucleotide fragments were precipitated, and all glassware was cleaned to remove any traces of RNase as described in the following section entitled "Inactivation of RNases on Equipment, Supplies, and in Solutions." All solutions were stored in RNAase free glassware and introduction of nucleases was prevented. Absolute ethanol was stored at 0° C. until used. Micropipettes were used to add two volumes of ice cold ethanol to nucleic acids that were to be precipitated in microcentrifuge tubes. Capped microcentrifuge tubes were placed into the microfuge and spun at 15,000×g for 15 minutes. The supernatant was discarded and precipitated RNA was re-dissolved in DEPC treated DI-water. RNA was stored at 4° C. in microcentrifuge tubes until ready to use.

Ligation of RNA Fragments 2 and 3

All glassware was cleaned to remove any traces of RNase as described in the following section entitled "Inactivation of RNases on Equipment, Supplies, and in Solutions." The following was added to a new 1.5 ml polypropylene snap capped microcentrifuge tube using a 100-1000 µl pipette and a new sterile pipette tip was used for each solution:

| | |
|---|---|
| Fragment 2 (3.0 nM) | 125.0 µl |
| Fragment 3 (3.0 nM) | 125.0 µl |
| Reaction buffer | 250.0 µl |
| RNA T4 ligase (9-12 U/ml) | 42 µl |
| Reaction Buffer | |
| RNase free DI-water | 90.00 ml |
| Tris-HCl (50 mM) | 0.79 g |
| MgCl2 (10 mM) | 0.20 g |
| DTT (5 mM) | 0.078 g |
| ATP (1 mM) | 0.55 g |
| pH to 7.8 with HCL | QS to 100.00 ml |
| RNase free DI-water | |

The mixture was gently mixed and the RNA was melted by incubating the mixture at 16° C. for one hour in a temperature controlled refrigerated chamber. RNA was precipitated out of the solution immediately after the incubation was completed.

Alcohol Precipitation

Two volumes (~1000 µl) of ice cold absolute ethanol were added to the reaction mixture. The microcentrifuge tube was placed in a microcentrifuge at 15,000×g for 15 minutes. The supernatant was decanted and discarded and the precipitated RNA was re-dissolved in 100 µl DEPC treated water. The mixture was electrophoresed as described in the following section entitled "Polyacrylamide Gel Electrophoresis (PAGE) of Psoralenated RNA Fragments." The following was the order of rate of migration for each fragment in order from fastest to slowest:

```
a) Frag. 2
   5'CUAGAΨCUGGAGG3'-OHPsoralen         (SEQ ID NO: 5)

b) Frag. 3
   5'UCCUGUGTΨCGAUCCACAGAAUUCGCACC-     (SEQ ID NO: 6)
   Puromycin c) Frag 2 + 3
   5'CUPsoralenAGAYCUGGAGGUCCUGUGTΨC    (SEQ ID NO: 7)
   GAUCCACAGAAUUCGCACC Puromycin
```

Each fraction was isolated by UV shadowing, the bands were cut out, the RNAs were eluted from the gels and the RNA elute was precipitated out as described in the following section entitled "Polyacrylamide Gel Electrophoresis (PAGE) of Psoralenated RNA Fragments." The ligation procedure was repeated with any residual unligated fragment 2 and 3 fractions. The ligated fractions 2 and 3 were pooled and stored in a small volume of RNase free DI-water at 4° C.

Ligation of RNA Fragment 1 with Fragment 2+3

All glassware was cleaned to remove any traces of RNase as described in the following section entitled "Inactivation of RNases on Equipment, Supplies, and in Solutions." The following was added to a new 1.5 ml polypropylene snap capped microcentrifuge tube. A 100-1000 µl pipette and new tip was used for each solution:

| | |
|---|---|
| Fragment 2 + 3 (3.0 nM) | 125.0 µl |
| Reaction buffer | 250.0 µl |
| T4 Polynucleotide Kinase(5-10 U/ml) | 1.7 µl |
| Reaction Buffer | |
| RNase free DI-water | 90.00 ml |
| Tris-HCl (40 mM) | 0.63 g |
| MgCl2 (10 mM) | 0.20 g |
| DTT (5 mM) | 0.08 g |
| ATP (1 mM) | 0.006 g |
| pH to 7.8 with HCL | QS to 100.00 ml |
| RNase free DI-water | |

The RNA was gently mixed then melted by heating the mixture to 70° C. for 5 minutes in a heating block. The mixture was cooled to room temperature over a two hour period and the RNA was allowed to anneal in a tRNA configuration. The RNA was precipitated out of the solution.

Alcohol Precipitation

Two volumes (~1000 µl) of ice cold absolute ethanol were added to the reaction mixture. The microcentrifuge tube was placed in a microcentrifuge at 15,000×g for 15 minutes. The supernatant was decanted and discarded and the precipitated RNA was re-dissolved in 100 µl DEPC treated water. The mixture was electrophoresed as described in the following section entitled "Polyacrylamide Gel Electrophoresis (PAGE) of Psoralenated RNA Fragments." The following was the order of rate of migration for each fragment in order from fastest to slowest:

a) Frag. 1
    5'GCGGAUUUAGCUCAGUUGGGAGAGCGCCAGA (SEQ ID NO: 8)
    CU3' b) Frag 2 + 3
    5'CUPsoralenAGAYCUGGAGGUCCUGUGTΨC (SEQ ID NO: 6)
    GAUCCACAGAAUUCGCACCPuromycin c) Frag. 1 + 2 + 3
    5'GCGGAUUUAGCUCAGUUGGGAGAGCGCCAGA (SEQ ID NO: 9)
    CUCUPsoralenAGAΨCUGGAGGUCCU-
    GUGTΨCG
    AUCCACAGAAUUCGCACCPuromycin Each fraction was isolated by UV shadowing, the bands were cut out, the RNAs were eluted from the gels and the RNA elute was precipitated out as described in the following section entitled "Polyacrylamide Gel Electrophoresis (PAGE) of Psoralenated RNA Fragments." The ligation procedure was repeated with the unligated Fragment 1 and the 2+3 Fraction. The ligated fractions 2+3 were pooled and stored in a small volume of RNase free DI-water at 4° C.

Final RNA Ligation

The following was added to a new 1.5 ml polypropylene snap capped microcentrifuge tube. A 100-1000 µl pipette and new tip was used for each solution:

| Fragment 1 + 2 + 3 (3.0 nM) | 250 µl |
| reaction buffer | 250 µl |
| RNA T4 ligase (44 µg/ml) | 22 µg |

The mixture was incubated at 17° C. in a temperature controlled refrigerator for 4.7 hours. Immediately after the incubation the tRNA was precipitated out as described in step 6.2 above and the tRNA was isolated by electrophoresis as described in the following section entitled "Polyacrylamide Gel Electrophoresis (PAGE) of Psoralenated RNA Fragments." The tRNA was pooled in a small volume of RNase free water and stored at 4° C. for up to two weeks or stored at −20° C. for periods longer than two weeks.

Polyacrylamide Gel Electrophoresis (Page) of Psoralenated RNA Fragments

Acrylamide Gel Preparation

All reagents and glassware were made RNAase free as described in the following section entitled "Inactivation of RNases on Equipment, Supplies, and in Solutions." The gel apparatus was assembled to produce a 4 mm thick by 20 cm×42 cm square gel. 29 parts acrylamide with 1 part ammonium crosslinker were mixed at room temperature with the appropriate amount of acrylamide solution in an RNAase free, thick walled Erlenmeyer flask.

| Acrylamide Solution | |
| --- | --- |
| urea (7M) | 420.42 g |
| TBE (1X) | QS to 1 L |
| 5X TBE | |
| 0.455 M Tris-HCl | 53.9 g |
| 10 mM EDTA | 20 ml of 0.5 M |
| RNAase free DI water | 900 ml |
| pH with boric acid to | pH 9 |
| QS with RNAase free DI water to | 1 L |

The mixture was degassed with vacuum pressure for one minute. The appropriate amount of TEMED was added, mixed gently, and then the gel mixture was poured between the glass plates to within 0.5 cm of the top. The comb was immediately inserted between the glass sheets and into the gel mixture. An RNAase free gel comb was used. The comb produced wells for a 5 mm wide dye lane and 135 mm sample lanes. The gel was allowed to polymerize for about 30-40 minutes then the comb was carefully removed. The sample wells were rinsed out with a running buffer using a micropipette with a new pipette tip. The wells were then filled with running buffer.

Sample Preparation

An aliquot of the sample was suspended in loading buffer in a snap capped microcentrifuge tube and vortex mixed. Indicator dye was not added to the sample.

| Loading Buffer | |
| --- | --- |
| Urea (7M) | 420.42 g |
| Tris HCl (50 mM) | 7.85 g |
| QS with RNAase free D-H2O | to 1 L |

Eletrophoresis Run

The maximum volume of RNA/loading buffer solution was loaded into the 135 mm sample wells and the appropriate volume of tracking dye in 5 mm tracking lane. The samples were electrophoresed in a 5° C. refrigerator. The electrophoresis was stopped when the tracking dye reached the edge of the gel. The apparatus was then disassembled. Glass panels were not removed from the gel. The gel-glass panel unit was placed on a UV light box. With UV filtering goggles in place, the UV lights were turned on. The RNA bands were identified. They appeared as denser shadows under UV lighting conditions. The RNA was extracted from the gel. Each band was excised with a new sterile and RNAase free scalpel blade and each band was transferred into a new 1.5 ml snap capped microcentrifuge tube. Each gel was crushed against the walls of the microcentrifuge tubes with the side of the scalpel blade. A new blade was used for each sample. 1.0 ml of 0.3M sodium acetate was added to each tube and eluted for at least 24 hours at 4° C. The eluate was transferred to a new 0.5 ml snap capped polypropylene microcentrifuge tubes with a micropipette with a new RNAase free pipette tip for each tube. Two volumes of ice cold ethanol was added to each eluate, then centrifuged at 15,000×g for 15 minutes in a microcentrifuge. The supernatants were discarded and the precipitated RNA was redissolved in 100 µl of DEPC treated DI water. The RNA was stored in the microcentrifuge tubes at 4° C. until needed.

Oligonucleotide Analysis by HPLC

HPLC purification of the RNA oligonucleotides was performed using anion exchange chromatography. Either the 2'-protected or 2'-deprotected forms may be chromatographed. The 2'-protected form offered the advantage of minimizing secondary structure effects and providing resistance to nucleases. If the RNA was fully deprotected, sterile conditions were required during purification.

One skilled in the art will understand that the HPLC purification methods of Example 2 may be modified in order to purify the RNA oligonucleotides. Modification of the HPLC purification methods of Example 2, including HPLC gradient, temperature, and other parameters, may be necessary. One of skill in the art would also recognize that a one-step HPLC purification method may also be used in accordance with several embodiments of the current invention.

Inactivation of RNAses on Equipment, Supplies, and in Solutions

Glassware was treated by baking at 180° C. for at least 8 hours. Plasticware was treated by rinsing with chloroform. Alternatively, all items were soaked in 0.1% DEPC.

Treatment with 0.1% DEPC 0.1% DEPC was prepared. DI water was filtered through a 0.2 µM membrane filter. The water was autoclaved at 15 psi for 15 minutes on a liquid cycle. 1.0 g (wt/v) DEPC/liter of sterile filtered water was added.

Glass and Plasticware

All glass and plasticware was submerged in 0.1% DEPC for two hours at 37° C. The glassware was rinsed at least 5× with sterile DI water. The glassware was heated to 100° C. for 15 minutes or autoclaved for 15 minutes at 15 psi on a liquid cycle.

Electrophoresis Tanks used for Electrophoresis of RNA

Tanks were washed with detergent, rinsed with water then ethanol and air dried. The tank was filled with 3% (v/v) hydrogen peroxide (30 ml/L) and left standing for 10 minutes at room temperature. The tank was rinsed at least 5 times with DEPC treated water.

Solutions

All solutions were made using Rnase free glassware, plastic ware, autoclaved water, chemicals reserved for work with RNA and RNase free spatulas. Disposable gloves were used. When possible, the solutions were treated with 0.1% DEPC for at least 12 hours at 37° C. and then heated to 100° C. for 15 minutes or autoclaved for 15 minutes at 15 psi on a liquid cycle.

RNA Translation

2 µl of gastroinhibitory peptide (GIP) mRNA at a concentration of 20 µl/ml was placed in a 250 µl snapcap polypropylene microcentrifuge tube. 35 µl of rabbit reticulocyte lysate (available commercially from Promega) was added. 1 µl of amino acid mixture which did not contain methionine (available commercially from Promega) was added. 1 µl of $^{35}$S methionine or unlabeled methionine was added. 2 µl of $^{32}$P GIP mRNA or unlabeled GIP mRNA was added. Optionally, 2 ml of luciferase may be added to some tubes to serve as a control. In a preferred embodiment, luciferase was used instead of GIP mRNA. One skilled in the art will understand that indeed any mRNA fragment containing the appropriate sequences may be used.

SATA was added to the experimental tubes. Control tubes which did not contain SATA were also prepared. The quantity of SATA used was approximately between 0.1 µg to 500 µg, preferably between 0.5 µg to 50 µg. 1 µl of Rnasin at 40 units/ml was added. Nuclease free water was added to make a total volume of 50 µl.

For proteins greater than approximately 150 amino acids, the amount of tRNA may need to be supplemented. For example, approximately 10-200 µg of tRNA may be added. In general, the quantity of the SATA should be high enough to effectively suppress stop or pseudo stop codons. The quantity of the native tRNA must be high enough to out compete the SATA which does not undergo dynamic proofreading under the action of elongation factors.

Each tube was immediately capped, parafilmed and incubated for the translation reactions at 30° C. for 90 minutes. The contents of each reaction tube was transferred into a 50 µl quartz capillary tube by capillary action. The SATA was crosslinked with mRNA by illuminating the contents of each tube with 2-10 J/cm2 ~350 nm wavelength light, as per Gasparro et al. (Photochem. Photobiol. 57:1007 (1993), herein incorporated by reference). Following photocrosslinking, the contents of each tube were transferred into a new snapcap microfuge tube. The ribosomes were dissociated by chelating the calcium cations by adding 2 µl of 10 mM EDTA to each tube. Between each step, each tube was gently mixed by stirring each component with a pipette tip upon addition.

The optimal RNA for a translation was determined prior to performing definitive experiments. Serial dilutions may be required to find the optimal concentration of mRNA between 5-20 µg/ml.

SDS-Page electrophoresis was performed on each sample, as described above. Autoradiography on the gel was performed, as described by Sambrook et. al., Molecular Cloning, A Laboratory Manual, $2^{nd}$ ed., Coldspring Harbor Press (1989), herein incorporated by reference.

The above example teaches the production and use of SATA (e.g., puromycin on tRNA plus crosslinker on the tRNA) and the production and use of Linking tRNA Analog (e.g., no puromycin, but has crosslinker on tRNA).

In another example, the SATA was produced in a manner similar to the above methodology, except that uridines were substituted with pseudouridines. Substitution by pseudouridines can also be used with Linking tRNA Analog, as it facilities the formation of crosslinker monoadduct formation (such as formation of the psoralen monoadduct). This technique is discussed below in Example 2.

EXAMPLE 2

Production of the SATA Using Pseudouridine

As discussed above, one skilled in the art will appreciate that the SATA, Linking tRNA Analog and Nonsense Suppressor tRNA can be produced in a number of different ways. FIG. 5 shows the chemical structures for uridine and pseudouridine. Pseudouridine is a naturally occurring base found in tRNA that forms hydrogen bonds just as uridine does, but lacks the 5-6 double bond that is the target for psoralen. Pseudouridine, as used herein, shall include the naturally occurring base and any synthetic analogs or modifications. In a preferred embodiment, the SATA was produced using pseudouridine. Linking tRNA Analog can also be produced using pseudouridine. Specifically, in a preferred embodiment, three fragments (FIG. 1) were purchased from a commercial source (Dharmacon Research Inc., Boulder, Colo.). Modified bases and a fragment 3 ("Fragment 3") with a pre-attached puromycin on its 3' end and a $PO_4$ on its 3' end were included, all of which are available commercially. The three fragments were used to facilitate manipulation of a fragment 2 ("Fragment 2") in forming the monoadduct. Sequences of the three fragments, according to some embodiments, are as follows (2 example sequences are provided for each fragment):

```
Fragment 1
5'PO₄GCGGAUUUAGCUCAGUUGGGAGAGCGCCA    (SEQ ID NO: 10)
GACOH3'

5'PO₄GCGGAUUUAGCUCAGUUGGGAGAGCGCCA    (SEQ ID NO: 16)
GACOH3'

Fragment 2
5'OHΨCUAACΨCOH3'                      (SEQ ID NO: 11)

5'OHΨCUAAAΨCOH 3'                     (SEQ ID NO: 17)
```

-continued

Fragment 3
5'PO₄UGGAGGUCCUGUGTΨCGAUCCACAGAAUU (SEQ ID NO: 12)
CGCACCPuromycin3'

5'PO₄UGGAGGUCCUGUGTΨCGAUCCACAGAAUU (SEQ ID NO: 18)
CGCACCPuromycin3'

The above sequences listed in Fragment 3 are applicable for SATA. For Linking tRNA Analogs, the sequences would be similar, except the puromycin would be replaced by adenosine.

Modified yeast tRNAAla or yeast tRNAPhe was used according to one embodiment of the invention. However, one skilled in the art will understand that sequences can be chosen widely from known tRNAs or by selecting sequences that will form into a tRNA-like structure. One advantage of using pseudouridine in some embodiments is that the pseudouridine in Fragment 2 avoids psoralen labeling of the nontarget U's. Use of pseudouridine instead of uridine decreases the avidity of the A site of the ribosome for the tRNA analog but eliminates the interaction of the terminal uridine with psoralen. The use of the Yarus "extended anticodon" guidelines increases A site binding (Yarus, Science 218:646-652, 1982, herein incorporated by reference).

In one embodiment, Fragment 2 was used in a helical conformation to induce the psoralen to intercalate. One skilled in the art will understand that other conformations can also be used in accordance with several embodiments of the invention. A complementary strand was also used. RNA or DNA was used, and a sequence, such as poly C or poly G when C interacts with the psoralen to one or both ends, was added to facilitate separation and removal after monoadduct formation was accomplished. Use of pseudouridine instead of uridines in the complement permitted the use of a high efficiency wave length, such as about 365 nm, without fear of crosslinking the product. Irradiation was preferably in the range of about 300-450 nm, more preferably in the range of about 320 to 400 nm, and most preferably about 365 nm. Further, use of pseudouridine left the furan-sided monoadduct in place on Fragment 2 because the Maf is the predominate first step in the crosslink formation.

The following cRNA sequences with pseudouridine were used according to a preferred embodiment of the present invention. One skilled in the art will understand that substitutions and modifications of these sequences, and of the other sequences listed herein, can also be used in accordance with several embodiments of the current invention. For example, for SEQ ID NO: 19, listed below, the sequence can also be

```
5'XXXXXXGAΨΨΨAGAXXXXXXX3':   (SEQ ID NO: 30)

CCCΨCCAGAGΨΨAGACCC            (SEQ ID NO: 13)

5'CCCCCCGAΨΨΨAGACCCCCCC3'     (SEQ ID NO: 19)
```

Step 1: Furan Sided Monoadduction of Psoralen to Fragment 2

The formation of a furan sided psoralen monoadduct with the target uridine of Fragment 2 was performed as follows:

A reaction buffer was prepared as follows:

| Tris HCL | 25 mM |
|---|---|
| NaCl | 100 mM |
| EDTA | 0.32 mM |
| pH | 7.0 |

4'hydroxy methyl-4,5',8'-triethyl psoralen (HMT) was then added to a final concentration of 0.32 mM and equimolar amounts of fragment 2 and cRNA were added to a final molar ratio of fragment 2: cRNA : psoralen=1:1:1000. A total volume of 100 µl was irradiated at a time.

The mixture of complementary oligos, HMT, psoralen was processed as follows:

1) Heated to 85° C. for 60 sec followed by cooling to 4° C. over 15 min, using PCR thermocycler.
2) Irradiated for 20 min at 4° C., in Eppendorf UVette plastic cuvette, covered top with parafilm, laid on the top of UV lamp (1 mW/cm² multi-wavelength UV lamp (λ>300 nm) (UV L21 model λ 365 nm).

Steps 1 and 2 above were repeated 4 times to re-intercalate and irradiate HMT. After the second irradiation additional 10 µl of 1.6 mM HMT was added in total 100 µl reaction volume. After 4 cycles of irradiation, the free psoralens were extracted with chloroform and all oligos (labeled and unlabeled) were precipitated with ethanol overnight (see precipitation step). A small aliquot was saved for gel identification.

Step 2: Purification of HMT Conjugated Fragment 2 (2MA) Oligo by HPLC

1) The reaction mixture was dried with speed vacuum for 10 minutes and then was dissolved with 2 µl of 0.1 M TEAA, pH 7.0 buffer.

| 0.1 M TEAA, pH 7.0 Buffer | |
|---|---|
| Acetic Acid | 5.6 ml |
| Triethylamine | 13.86 ml |
| H₂O (RNAase free) | 950 ml |
| pH adjusted to 7.0 with acetic acid and water added to 1 L | |

2) The sample was loaded onto a Waters Xterra MS C18, 2.5 µm, 4.5×50 mm reverse-phase column pre-equilibrated with buffer A (5% wt/wt acetonitrile in 0.1M TEAA, pH 7.0) The sample was eluted with a gradient of 0-55% buffer B (15% wt/wt acetonitrile in 0.1M TEAA, pH 7.0) to buffer A over a 35 minute time frame at a flow rate of 1 ml/minute. The column temperature was 60° C. and the detection wave length, set by a narrow band filter, was 340 nm. Furan sided psoralen monoadduct absorbs at 340 nm but the RNA, and any pyrone sided monoadduct does not. The buffer solutions were filtered and degassed before use.

The 2MA eluted at around 25-28 minutes at a buffer B concentration of 40%. Unpsoralenated fragment 2 eluted before 8 minutes based on subsequent gel electrophoresis analysis on collected fractions.

The column was washed with 100% acetonitrile for 5 minutes and was re-equilibrated with buffer A for 15 minutes. All fractions were dried with speed vacuum overnight.

The fractions containing the 2MA were identified by the level of absorbance at 260 nm (RNA) and 330 nm (furan sided psoralen monoadducted RNA). This was done by redissolving the dried fractions with 120 µl of Rnase-free distilled water and the absorbance was measured with a spectrophotometer at 260 nm and 330 nm. The fractions with high absorbance at both wavelengths were pooled then dried with speed vacuum. A small aliquot from each was saved for gel analysis.

The cross-linked products were analyzed on a denaturing 20% TBE-urea gel and visualized by gel silver staining.

Step 3: Purification of HMT Conjugated Fragment 2 Oligo from cRNA by HPLC

The dried samples were pooled and then were dissolved with 0.5×TE buffer. A sample of about 0.4 absorbance unit was loaded onto a Dionex DNAPac PA-100 (4×250 mm) column which was pre-equilibrated with buffer C (25 mM Tris-HCl, pH 8.0) and the column temperature was 85° C. (anion exchange HPLC).

The oligos were eluted at a flow rate of 1 ml/min with a concave gradient from 4% to 55% buffer D for 15 minutes followed by a convex gradient from 55% to 80% with buffer D for the next 15 minutes. The oligos were washed with 100% buffer D for 5 min and 100% buffer C for another 5 min at a flow rate of 1.5 ml/min; Fractions were collected that absorbed 260 nm light. 2MA had a retention time (RT) of 16.2 minutes and was eluted by 57% buffer D, and free fragment 2 had RT less than 16.6 minutes, and was eluted by 55% buffer D and free cRNA had RT greater than 19.2 minutes. The fractions were collected that absorbed at 254 or 260 nm. The collected fractions were dried with speed vacuum overnight. All solutions were filtered and degassed before use.

The solution used comprised the following:
C: 25 mM Tris-HCl pH 8.0;
D: 250 mM NaClO4 in 25 mM Tris pH 8.0 buffer.
TE: 10 mM Tris-HCl pH 8.0 with 1 mM EDTA Step 4: Desalting, Precipitation and Collection of the Purified 2MA Oligo The dried fractions were redesolved with 100µl Rnase free distilled water. 500 µl cool 100% ethanol with 0.5M (NH4)2CO3 was added and the mixture was vortexed briefly. The mixture was then frozen on dry ice for 60 minutes or stored at −20° C. overnight.

The samples were then brought to 4° C. and centrifuged at maximum speed in a microcentrifuge for 15 minutes. The position of the pellet was noted and the supernatant was decanted or removed by pipette. Care was taken not to disturb pellet. If the pellet still contained salt, this step was repeated. The pellet was then washed with 70% pre-cooled ethanol twice. The wet pellet was dried with speed vacuum for 15 min. Urea PAGE gel identified the right fractions for the next step.

Step 5: Ligation of 2MA Oligo to Fragment 3 Oligo

The following steps were performed:
A. The Following Reagents and Instruments were Used:
Nuclease-Free Water (Promega)
polyethylene glycol (PEG8000 Sigma) 40%(wt/wt in water)
RNasin® Ribonuclease Inhibitor (Promega)
phenol:chloroform
1.5 ml sterile microcentrifuge tubes
100% ethanol
70% ethanol
Dry ice or −20° C. freezer
Microcentrifuge at room temperature and +4° C.
PCR thermocycler or water bath
B. The Following Reaction Conditions were Used:
50 mM Tris-HCl (pH 7.8)
10 mM MgCl2,
10 mM DTT
1 mM ATP
18-20% PEG
C. The Following Reaction Mixture was Assembled in a Sterile Microcentrifuge Tube:
Fragment 3 (Donor) 1 µl (6µg) (Purified, when necessary, before using as a donor)
2MA (Acceptor) 1 µl (1.5 µg)

After adding 8 µl Rnase free dH2O 8 µl, the reactions were incubated at 85° C. for 1 minute to relax the oligo secondary structure, then slowly cooled to 4° C., using a PCR machine thermocycler. The preheated tube was placed on ice to keep cool and centrifuged briefly, then the following was added:

| 10X Ligase Buffer | 4 µl |
| 10 mM ATP | 4 µl |
| Rnase Out or Rnasin(40 u/µl) Promega | 0.5 µl |
| PEG, 40% (Sigma) | 20 µl |
| T4 RNA Ligase (10 u/µl) (NEB) | 1 µl |

Nuclease-free water was added to final Volume of 40 µl. The mixture was incubate at 16° C. overnight(16 hr). The mixture was centrifuged briefly and then was placed on ice.

D. Precipitation of Oligonucleotides:

60 µl DEPC RNase free distilled water was added to the mixture and then 150 µl phenol/chloroform was added. The mixture was vortexed vigorously for 30 seconds. The precipitate was then centrifuged out at maximum speed in a microcentifuge for 5 minutes at room temperature. The aqueous phase was transferred to a new microcentrifuge tube (>95 µl).

To this was added 3 µl 5 mg/ml glycogen, and 500 µl pre-cooled 100% ethanol with 0.5M (NH4)2CO3 and the mixture was vortexed briefly and then was frozen on dry ice for 60 minutes. At this point, it may be stored overnight at −20° C. The dried fractions were redissolved with 100µl Rnase-free distilled water, 500 µl cool 100% ethanol with 0.5M (NH4)2CO3 was added and vortexed briefly. This was then frozen on dry ice for 60 minutes or stored at −20 C overnight. The samples were then brought to 4° C. and centrifuged at maximum speed in a microcentrifuge for 15 minutes and supernatant removed by pipette. Care was taken not to disturb pellet. If the pellet still contained salt, this step was repeated once. The pellet was then washed with 70% precooled ethanol several times. This was then centrifuged at maximum speed in a microcentrifuge for 5 minutes at 4 C. The ethanol was carefully removed using a pipette. Centrifugation was repeated again to collect remaining ethanol which was carefully removed. The wet pellet was dried with speed vacuum for 10 min. A small aliquot was collected for the gel analysis. For long term storage, the RNA was stored in ethanol at −20 C. Care was taken not to store the RNA in DEPC water.

Step 6: Purification of the Ligated Fragment 3 Oligo Complex

The dried sample was redesolved with 0.5×TE buffer and was loaded onto a DNAPac PA-100 column which was equilibrated with buffer C. The column temperature was 85° C. and the detector operated at 254 nm to identify fractions with RNA and at 340 nm to identify fractions with 2MaF. The oligos were eluted with a convex gradient from 30% to 70% with buffer D for the first 20 minutes at a flow rate of 0.8 ml/min and followed with a linear gradient from 70% to 98% D for another 20 min at the same flow rate. The elution was completed by washing with 100% D for 7 min and 100% C for another 10 min at 1.0 ml/min flow rate. The fractions were detected with 254 or 260 nm wavelength light. The ligated oligos (2MA-fragment 3) were eluted after 34 min, by more than 90% buffer B. Fractions with 254 nm absorbance ($A_{254nm}$>0.01) were collected and dried with speed vacuum overnight.

Step 7: Purified 2MA-Fragment 3 Desalting and Precipitation

The dried fractions were re-dissolved with 100 µl Rnase free distilled water, 500 µl cool 100% ethanol with 0.5M (NH4)2CO3 was added and the mixture was vortexed briefly. The mixture was then frozen on dry ice for 60 minutes or stored at −20 C overnight.

The samples were brought to 4° C. and centrifuged at maximum speed in a microcentrifuge for 15 minutes. The position of the pellet was noted and the supernatant decanted or removed by pipette. Care was taken not to disturb pellet. If still containing salt, this step was repeated. The pellet was then washed with 70% pre-cooled ethanol twice. The wet pellet was dried with speed vacuum for 15 min.

Urea PAGE was performed to identify the ligated 2MA-fragment-3 for use in the next step of ligating fragment 1 to the 2MA-fragment-3 oligo which completes the SATA linker.

Step 8: Preparation of SATA (or Other tRNA Molecule)

A. RNA Oligo 5'phosphorylation

1. Reagent and Instrument:
   Nuclease-Free Water (Cat.# P1193 Promega)
   RNasin® Ribonuclease Inhibitor (Cat# N2511 Promega)
   Phenol:chloroform
   Sterile microcentrifuge tubes
   100% ethanol
   70% ethanol
   Microcentrifuge at room temperature and 4° C.
   PCR thermalcycler or water bath
2. Assemble the Following Reaction Mixture in a Sterile Microcentrifuge Tube:

| Component | Volume |
|---|---|
| Acceptor RNA | <200 ng |
| T4 ligase 10X Reaction Buffer* | 4 μl |
| RNasin ® Ribonuclease Inhibitor (40 u/μl) | 20 unit |
| T4 kinase (9-12 u/μl) | 2 μl |
| 10 mM ATP | 4 μl |
| Nuclease-Free Water to final volume | 40 μl |

Incubate at 37° C. for 30 minutes in a PCR thermocycler or water bath. For non-radioactive phosphorylation, use up to 300 pmol of 5' termini in a 30 to 40 μl reaction containing 1×T4 Polynucleotide Kinase Reaction Buffer, 1 mM ATP and 10 to 20 units of T4 Polynucleotide Kinase. Incubate at 37° C. for 30 minutes. 1×T4 DNA Ligase Reaction Buffer contains 1 mM ATP and can be substituted in non-radioactive phosphorylations. T4 Polynucleotide Kinase exhibits 100% activity in this buffer). Fresh buffer is required for optimal activity (in older buffers, loss of DTT due to oxidation lowers activity.

B. Annealing Fragment1 and 2MA-Fragment 3 Oligo Complex:

1. Reagents and Instruments:
   PCR thermocycler instrument or water bath
   100 μg/ml nuclease-free albumin
   100 mM MgCl2
2. Assemble the Following Reaction Mixture in a Sterile Microcentrifuge Tube:

| | |
|---|---|
| Acceptor RNA oligo (1E) | <200 ng |
| Donor RNA oligo (3G-2G ligated oligo) (5' phosphorylated oligo from step A) | <200 ng |

Appropriate ratios are as follows: Acceptor oligo:Donor oligo (Fragment 1: 2MA-Fragment 3) molar ratio should be 1:1.1 to avoid fragment 1 self-ligation. MgCl$_2$ was added to T4 ligase buffer (50 mM Tris-HCl, pH 7.8, 10 mM MgCl$_2$, 10 mM DTT and 1 mM ATP) to final 20 mM concentration. Add Rnase free albumin to final 5 μg/ml. The final volume should be no more than 100 μl. The solution was heated to 70° C. for 5 min, then was cooled from 70° C. to 26° C. over 2 hours and cooled from 26° C. to 0° C. over 40 minutes. Incubate at 16° C. for 16 to 17 hours using PCR instrument.

C. Ligation of Annealed Oligos

| | |
|---|---|
| Annealed oligos | <15 μl |
| 10 mM ATP | 2 μl |
| 40% PEG | 18 μl |
| T4 ligase 10X Buffer | 2 μl |
| RNasin ® Ribonuclease Inhibitor (40 u/μl) | 0.5 μl |
| T4 ligase (9-12 u/μl)(NEB) | 1 μl |
| Nuclease-Free Water to final volume | 40 μl |

D. Precipitating tRNA Fragment

After ligation, 50 μl DEPC water and 150 μl phenol: chloroform were added and vortexed vigorously for 30 seconds. This was then centrifuged at maximum speed in a microcentrifuge for 5 minutes at room temperature. The aqueous phase was transferred to a new microcentrifuge tube (~100 μl). To this was added 2 μl 10 mg/ml mussel glycogen, 10 μl 3M sodium acetate, pH 5.2. This was mixed well. Then 220 μl 95% ethanol was added and vortexed briefly. The mixture was then frozen on dry ice for 30 minutes. At this point the mixture may be stored over night at −20° C. or one may proceed. In one embodiment, the RNA should preferably not be stored in DEPC water, but in ethanol, at −20° C.

Then the samples were brought to 4° C. and centrifuged at maximum speed in a microcentrifuge for 15 minutes. The position of the pellet was noted and the supernatant decanted or removed by pipette. Care was taken not to disturb pellet. The pellet was then washed with 70% pre-cooled ethanol twice. After removing the ethanol, the wet pellet was dried with a speed vacuum for 15 min. The dried pellet was stored at −20° C., until the next step.

RNA Translation

A luciferase mRNA which was modified to have the stop codon corresponding to that recognized by the anticodon of the SATA ( in the present case UAG) was used in a standard Promega in vitro translation kit in the recommended 1 μl of concentration 1 μg/μl. One skilled in the art will understand that indeed any mRNA fragment containing the appropriate sequences may be used.

SATA was added to the experimental tubes. Control tubes which did not contain SATA were also prepared. The quantity of SATA used was approximately between 0.1 μg to 500 μg, preferably between 0.5 μg to 50 μg. 1 μl of Rnasin at 40 units/ml was added. Nuclease free water was added to make a total volume of 50 μl.

For proteins greater than approximately 150 amino acids, the amount of tRNA may need to be supplemented. For example, approximately 10-200 μg of tRNA may be added. In general, the quantity of the SATA should be high enough to effectively suppress stop or pseudo stop codons. The quantity of the native tRNA must be high enough to out compete the SATA which does not undergo dynamic proofreading under the action of elongation factors.

Each tube was immediately capped, parafilmed and incubated for the translation reactions at 30° C. for 90 minutes. The contents of each reaction tube was transferred into a 50 μl quartz capillary tube by capillary action. The SATA was crosslinked with mRNA by illuminating the contents of each tube with 2-10 J/cm2 ~350 nm wavelength light, as per Gasparro et al. (Photochem. Photobiol. 57:1007 (1993), herein incorporated by reference). Following photocrosslinking, the contents of each tube were transferred into a new snapcap microfuge tube. The ribosomes were dissociated by chelating the calcium cations by adding 2 µl of 10 mM EDTA to each tube. Between each step, each tube was gently mixed by stirring each component with a pipette tip upon addition.

The optimal RNA for a translation was determined prior to performing definitive experiments. Serial dilutions may be required to find the optimal concentration of mRNA between 5-20 µg/ml.

SDS-Page electrophoresis was performed on each sample, as described above. Autoradiography on the gel was performed, as described by Sambrook et al., Molecular Cloning, A Laboratory Manual, $2^{nd}$ ed., Coldspring Harbor Press (1989), herein incorporated by reference.

The above example is instructive for the production and use of SATA (puromycin on tRNA and crosslinker on tRNA) and for the production and use of Linking tRNA Analog (no puromycin, with crosslinker on tRNA).

EXAMPLE 3

Production of Linking tRNA Analog Using Ribonucleotides Modified to from Crosslinkers: Use of Psoralen and Non-Psoralen Crosslinkers As described above, pseudouridine can be used in some embodiments to minimize the formation of unwanted monoadducts and crosslinks. In one embodiment, a crosslinker modified mononucleotide is formed and used. One advantage of the crosslinker modified mononucleotide is that it minimizes the formation of undesirable monoadducts and crosslinks.

As discussed above, one skilled in the art will appreciate that the SATA, Linking tRNA Analog, and Nonsense Suppressor Analog can be produced in a number of different ways. In a preferred embodiment, psoralenated uridine 5' mononucleotide, 2-thiocytosine, 2-thiouridine, 4-thiouridine 5-iodocytosine, 5-iodouridine, 5-bromouridine or 2-chloroadenosine can be produced or purchased and enzymatically ligated to an oligonucleotide to be incorporated into a tRNA analog. Aryl azides, and analogues of aryl azides, and any modifications thereto, can also be used in several embodiments, as a linking moiety or agent. The following protocol can be employed for crosslinkers that are located on the tRNA. One skilled in the art will understand that this protocol can also be used for crosslinkers located on the mRNA. Thus, the following example is instructive on the production and use of SATA, Linking tRNA Analog, and Nonsense Suppressor Analog.

Production of Modified Nucleotide 4-thioU, 5-iodo and 5-bromo U with and without puromycin can be purchased already incorporated into a custom nucleotide up to 80 basepairs in length (Dharmacon, Inc). Therefore, the SATA, and the Linking tRNA Analog with these crosslinkers already in place, and similar crosslinkers, can be purchased directly from Dharmacon, Inc. Nonsense Suppressor Analog can also be purchased from Dharmacon, Inc.

2-thiocytosine, 2-thiouridine, 4thiouridine 5-iodocytosine, 5-iodouridine, 5-bromouridine or 2-chloroadenosine can all be purchased for crosslinking from Ambion, Inc. for the use in the Ambion MODIscript kit for incorporation into RNA. Therefore, the SATA and the Linking tRNA Analog along with these crosslinkers, and similar crosslinkers, can be purchased directly from Ambion, Inc The $PO_4U_{psoralen}$ can be produced as follows:

```
AUAUAUAUAUAUAUAUAUAUAUGGGGGG (seq     (SEQ ID NO: 20)
A1)
(available from Dharmacon, Inc.)

CCCCCCATATATATATATATATATAT (seq       (SEQ ID NO: 21)
A2)
(available from University of Southern California
services).
```

The formation of a furan-sided psoralen monoadduct with the target uridine is performed as follows:

A reaction buffer is prepared. The reaction buffer, with a pH of 7.0, contains 25 mM Tris HCL, 100 mM NaCl, and 0.32 mM EDTA.

4'hydroxy methyl-4,5',8'-triethyl psoralen (HMT) is then added to a final concentration of 0.32 mM and equimolar amounts of seq A1 and seq A2 are added to a final molar ratio of seq A1 : seq A2 : psoralen=1:1:1000. A total volume of 100 µl is irradiated at a time.

The mixture of complementary oligos, HMT, trimethylpsoralen is processed as follows: 1) Heat to 85° C. for 60 sec followed by cooling to 4° C. over 15 min, using PCR thermocycler; and 2) Irradiate for 20 to 60 min at 4° C., in Eppendorf UVette plastic cuvette, covered top with parafilm, in an RPR-200 Rayonet Chamber Reactor equipped with a cooling fan and 419 nm wave. This is either placed on an ice water bath or in a -20° C. freezer.

Steps 1 and 2 above are repeated 4 times to re-intercalate and irradiate HMT. After 4 cycles of irradiation, the free psoralens are extracted with chloroform and all oligos (labeled and unlabeled) are precipitated with ethanol overnight (see precipitation step). A small aliquot is saved for gel identification.

Comparable sequences can be produced using the Ambion, Inc kit for non-psoralen crosslinkers.

RNase H Digestion of RNAs in DNA/RNA Duplexes

The following steps are performed: (1) Dry down oligos in speed vac; (2) Resuspend pellet in 10 µL 1×Hyb Mix; (3) Heat at 68° C. for 10 minutes; (4) Cool slowly to 30° C. Pulse spin down; (5) Add 10 µL 2×RNase H Buffer. Mix. (6) Incubate at 30° C. for 60 minutes; (7) Add 130 µL Stop Mix.

For the Phenol/Chloroform extract: (1) Add 1 vol. phenol/chloroform; (2) Vortex well; (3) Spin down 2 minutes in room temperature microfuge; (4) Remove top layer to new tube.

For the Chloroform extract: (1) Add 1 vol. chloroform; (2) Vortex well; (3) Spin down 2 minutes in room temperature microfuge; (4) Remove top layer to new tube.

Then, (1) Add 375 µL 100% ethanol; (2) Freeze at -80° C.; (3) Spin down 10 minutes in room temperature microfuge; (4) Wash pellet with 70% ethanol; (5) Resuspend in 10 µL loading dye; (6) Heat at 100° C. for 3 minutes immediately before loading.

Purification of monoribonucleotides nucleotides from the longer cDNA as well as longer RNA fragments, is accomplished using anion exchange HPLC. The psoralen-monoadducted mononucleotides ($PO_4U_{psoralen}$) are then separated by reverse phase HPLC from mononucleotides that were not monoadducted ($PO_4U$ and $PO_4A$).

Similar digestion techniques and nucleotide incorporation, described below, can also be used for non-psoralen crosslinkers using the Ambion, Inc kit.

Incorporation of Light Sensitive Nucleotides into the TRNA Component Oligoribonucleotides The following protocol can be used for incorporating a $pU_{crosslinker}$ into a CUA stop anticodon. However, one skilled in the art will understand that other nucleotides can also be used to produce other stop anticodons and pseudo stop anticodons in accordance with the methods described herein Generally, methods adapted from the protocols for T4 RNA ligase are used, but with some modification because of the lack of protection of the 3' OH of the modified nucleotides.

5'OH CUC OH 3' oligoribonucleotides (seq B1) can be purchased from Dharmacon, Inc. and can be as acceptors in the ligation. The molar ratio of B1 to psoralenated mononucleotides is preferably kept at 10:1 to 50:1 so that the modified U's will be greatly out-numbered, thereby preventing the formation of $CUC(U_{crosslinker})_N$. This makes one of the preferred reactions:

$CUC+pU_{psoralen} \rightarrow CUCU_{psoralen}$

In one embodiment, the product is purified by sequential anion exchange and reversed phase HPLC to ensure that the psoralenated U and the longer psoralenated 7 mer are separated. The 7 mer is then 3' protected by ligation with pAp yielding $CUCU_{crosslinker}Ap$ (Fragment 2B).

This is again purified with anion exchange HPLCF or the next ligation.

First Ligation of Fragment 2B to 1B or 1B1

This 2B fragment can be used in a tRNA analog that has a stable acceptor or one that has a native esterified acceptor. In one embodiment, to assure that the native 3' end can be aminoacylated by native AA-tRNA synthetases, the acceptor stem is modified in that version of the analog. In the SATA version, in one embodiment, the 3' fragment is maintained with a commercially prepared puromycin as the acceptor. Thus, in one embodiment, the following are used in two different 5' ends:

```
5' OHGCGGAUUUAGCUCAGUUGGGAGAGCGCCA (SEQ ID NO: 22)
GA 3' seq 1B
(to be used with the tRNA analog with the stable
puromycin acceptor) and 5' OHGGGGCUUUAGCUCAGUUGGGAGAGCGCCA (SEQ ID NO: 23)
GA 3' seq 1B₁
(to be used with the native esterified acceptor).
```

The ligation is performed again with T4 RNA ligase and purified by length. The equation for sequence 1B is as follows:

Ligation of the Two Half-Molecules of the TRNA Analog

The above product is treated with T4 polynucleotide kinase in two separate steps to remove the 3' phosphate and add a 5' phosphate.

The newly prepared 5' and 3' half molecules ends are then ligated generally following the previous protocols. The 3' sequences corresponding to the respective 5' sequences are as follows:

Sequence 1B: (ψ=pseudouridine)

```
5' PO₄GCGGAUUUAGCUCAGUUGGGAGAGCGCC (SEQ ID NO: 24)
AGACUCU_crosslinker A 3'
corresponded to the 3' half:

5' PO₄UGGAGGUCCUGUGTΨCGAUCCACAGAAU (SEQ ID NO: 31)
UCGCACCPur 3',
3B and sequence 1B1, 5' OHGGGGCUUUAGCUCAGUUGGGAGAGCGCCA (SEQ ID NO: 25)
GACUCU_crosslinker APO₄
corresponded to 3' half

5' PO₄UGGAGGUCCUGUGTΨCGAUCCACAGAAU (SEQ ID NO: 32)
CUCCACCA 3'.
```

The latter is recognizable by the aminoacyl tRNA synthetase for alanine in *E. coli*.

The example described above can be used to make and use the SATA, Linking tRNA, and the Nonsense Suppressor tRNA.

EXAMPLE 4

Placement of Crosslinkers on the mRNA for SATA and Nonsense Suppressor TRNA

In several embodiments, the crosslinker (such as psoralen or a non-psoralen crosslinker) is not placed on the tRNA, but rather located on the mRNA. For example, in one embodiment, the SATA comprises a puromycin located on the tRNA, while the crosslinker is on the mRNA. In yet another embodiment, the Nonsense Suppressor tRNA is used, and this comprises a tRNA with no puromycin, with the crosslinker being on the mRNA. Placement of the crosslinker on the message (the mRNA) can be accomplished as set forth below. The relevant sequence is as follows:

```
GGGUUAACUUUAGAAGGAGGUCGCCACCAUG   (SEQ ID NO: 26)
GUU AAA AUG AAA AUG AAA AUG AAA
AUG U_crosslinker AG
```

```
5' OHGCGGAUUUAGCUCAGUUGGGAGAGCGCCAGA 3' + CUCU_crosslinker APO₄ 3'    (SEQ ID NO: 22)→

5' OHGCGGAUUUAGCUCAGUUGGGAGAGCGCCAGACUCU_crosslinker APO₄ 3'          (SEQ ID NO: 24)
```

For sequence 1B₁:

```
5' OHGGGGCUUUAGCUCAGUUGGGAGAGCGCCAGA + CUCU_crosslinker APO₄ 3'       (SEQ ID NO:23) →

5' OHGGGGCUUUAGCUCAGUUGGGAGAGCGCCAGACUCU_crosslinker APO₄ 3'          (SEQ ID NO: 25)
```

For convenience only, and in one embodiment, a message with both Kozak and Shine Dalgarno sequences that has a large number of methionine codons for $^{35}$S labeling is used.

For 4-thiouridine, 5-bromouridine and 5-iodouridine, the message can be purchased fully-made from Dharmacon, Inc. For aryl azides, the method recited in Demeshkina, N, et al., RNA 6:1727-1736, 2000, herein incorporated by reference, can be used.

For 2-thiocytosine, 2-thiouridine, 5-iodocytosine, or 2-chloroadenosine, the modified bases can be purchased as the 5' monophosphate nucleotide from Ambion, Inc. When psoralen is used as the crosslinker, the modified 5' monophosphate nucleotide is made as above.

The modified 5' monophosphate nucleotides are first incorporated into hexamers to facilitate purification. The construction of uridine containing crosslinkers is shown but in several embodiments, the other bases can be incorporated into both stop and pseudo stop codons using similar techniques:

AUG+pUcrosslinker→AUGUcrosslinker was accomplished using a similar protocol described above, except a preponderance of AUG was used because of the absence of a 3' protection of the pNcrosslinker. The product was purified by anion exchange HPLC from the excess of AUG. Then 5' pAGbiotin 3' was added with T4 RNA ligase. The 3' biotin was simply a convenient 3' blocking group available form Dharmacon. The resulting AUGU$_{crosslinker}$AG$_{biotin}$ was again purified followed by 5' phosphorylation and ligated to:

```
GGGUUAACUUUAGAAGGAGGUCGCCACCAUGGUU (SEQ ID NO: 27)
AAAAUGAAAAUGAAAAUGAAA (sequence
M1)
``` to produce

```
GGGUUAACUUUAGAAGGAGGUCGCCACCAUGGNN (SEQ ID NO: 28)
AAAAUGAAAAUGAAAAUGAAAAUG
U_crosslinker AG_biotin.
```

The yield is high enough to obviate purification. Accordingly, using the protocol described above, SATAs and Nonsense Suppressor tRNAs can be made and used in accordance with several embodiments of the present invention.

EXAMPLE 5

Using TRNA Systems that do No Need Puromycin

Several embodiments of the present invention provide a system and method that do not require puromycin, puromycin analogs, or other amide linkers. In one embodiment, Linking tRNA Analogs and Nonsense Suppressor tRNAs do not require puromycin and can be made and used according to the following example.

For systems without puromycin, a translation system to aminoacylate the tRNA can be used. In other embodiments, aminoacylation can be accomplished chemically. One skilled in the art will understand how to chemically aminoacylate tRNA. Where translation systems are used, any type of translation system for aminoacylation can be employed, such as in vitro, in vivo and in situ. In one embodiment, am e-coli translation system is used. An *E. coli* translation system is used for systems with a tRNA modified to be recognized by the aaRS$^{Ala}$. In one embodiment, this is preferable for systems without the stable acceptor (e.g. the puromycin)

3 mcg of each of the following mRNA's are translated in 40 microliters each of Promega S30 *E. coli* translation mixture:

```
a) GGGUUAACUUUAGAAGGAGGUCGCCACCAUG (SEQ ID NO: 28)
   GUU AAA AUG AAA AUG AAA AUG AAA
   AUGUcrosslinkerAGbiotin
and b) GGGUUAACUUUAGAAGGAGGUCGCCACCAUG (SEQ ID NO: 29)
   GUU AAA AUG AAA AUG AAA AUG AAA
   AUGUAG
```

3 mcg of amber suppressor tRNA manufactured as above are added to the first. 3mcg of suppressor with crosslinker on the anticodon are added to the second. 35S-methionine is added to both and the mixtures are then incubated at 37° C. for 30 minutes. The reactions are then rapidly cooled by placement in an ice bath, transferred to a flat Petri dish and floated in an ice bath so that the mixture is 1.5 cm below a ~350 nm light source. They are exposed at ~20 J/cm for 15 min.

After irradiation, the mixtures are phenol extracted and ethanol precipitated. In this manner, systems such as the Linking tRNA Analogs and Nonsense Suppressor tRNAs are aminoacylated and used to connect the message (mRNA) to its coded peptide in accordance with several embodiments of the present invention.

EXAMPLE 6

Alternative Sequences

In a preferred embodiment, Fragments 1, 2 and 3, described above in Example 1, have the following alternate sequences:

```
Fragment 1 (SEQ ID NO: 13):
5' PO4 GCGGAUUUAGCUCAGUUGGGAGAGCGCCAGA N3-Methyl-U
3'

Fragment 2 (SEQ ID NO: 14):
5' UCUAAGΨCΨGGAGG 3'

Fragment 3-Unchanged from the sequence listed
above (SEQ ID NO: 6):
5' PO4 UCCUGUGTΨCGAUCCACAGAAUUCGCACC Puromycin 3'
```

Using the methods described above, the sequence of alternative Fragments 1+2+3 was (SEQ ID NO: 15):

```
5' PO4GCGGAUUUAGCUCAGUUGGGAGAGCGCCAGA(N3-
MethylU)UCUPsoralenAAGΨCΨGGAGGUCCUGUGTYCG
AUCCACAGAAUUCGPuromycin 3'
```

For Linking tRNA Analog and Nonsense Suppressor tRNA, the above sequences are similar, except adenosine is used to replace puromycin.

While a number of preferred embodiments of the current invention and variations thereof have been described in detail, other modifications and methods of use will be readily apparent to those of skill in the art. For all of the embodiments described above, the steps of the methods need not be performed sequentially. Accordingly, it should be understood that various applications, modifications and substitutions may be made without departing from the spirit of the invention or the scope of the claims.

What is claimed is:

1. A method for identifying and selecting a desired protein or nucleic acid molecule comprising:

providing an in vitro translation system;

providing at least two candidate mRNA molecules, wherein at least one of said mRNA molecules is untranslatable beyond a particular codon selected from the group consisting of a nonsense codon, a codon for which tRNAs having an anticodon complementary thereto are absent or substantially depleted in said in vitro translation system, and a codon located on a 3' end of a translatable reading frame of said mRNA molecule;

translating at least two of said candidate mRNA molecules in said in vitro translation system to generate at least one translated protein, wherein a tRNA molecule accepts a peptide chain and holds said chain in a manner such that ribosomal peptidyl transferase cannot detach it because the message in subsequent codons is untranslatable;

linking at least one of said candidate mRNA molecules to its corresponding translated protein at or near said particular codon via said tRNA molecule to form at least one cognate pair, wherein at least one of said candidate mRNA molecules is connected to said tRNA molecule by a crosslinker;

identifying one or more of said cognate pairs based upon the properties of said translated protein or said mRNA molecule, thereby identifying said desired protein or said desired nucleic acid molecule;

providing a plurality of said cognate pairs comprising said one or more identified cognate pairs, exposing said plurality of said cognate pairs to one or more binding agents; and selecting said desired protein or nucleic acid molecule based upon a reaction or lack of a reaction to said one or more binding agents;

wherein the crosslinker is selected from the group consisting of a sulfur-substituted nucleotide and a halogen-substituted nucleotide.

2. The method of claim 1, wherein said crosslinker is selected from the group consisting of one or more of the following: 2-thiocytosine, 2-thiouridine, 4-thiouridine, 5-iodocytosine, 5-iodouridine, 5-bromouridine and 2-chloroadenosine, and modifications or analogues thereof.

3. A method for identifying and selecting a desired protein or nucleic acid molecule comprising:

providing an in vitro translation system;

providing at least two candidate mRNA molecules, wherein at least one of said mRNA molecules is untranslatable beyond a particular codon selected from the group consisting of a nonsense codon, a codon for which tRNAs having an anticodon complementary thereto are absent or substantially depleted in said in vitro translation system, and a codon located on a 3' end of a translatable reading frame of said niRNA molecule;

translating at least two of said candidate mRNA molecules in said in vitro translation system to generate at least one translated protein, wherein a tRNA molecule accepts a peptide chain and holds said chain in a manner such that ribosomal peptidyl transferase cannot detach it because the message in subsequent codons is untranslatable;

linking at least one of said candidate mIRNA molecules to its corresponding translated protein at or near said particular codon via said tRNA molecule to form at least one cognate pair, wherein at least one of said candidate mRNA molecules is connected to said tRINA molecule by a crosslinker;

identifying one or more of said cognate pairs based upon the properties of said translated protein or said mRNA molecule, thereby identifying said desired protein or said desired nucleic acid molecule;

providing a plurality of said cognate pairs comprising said one or more identified cognate pairs, exposing said plurality of said cognate pairs to one or more binding agents; and selecting said desired protein or nucleic acid molecule based upon a reaction or lack of a reaction to said one or more binding agents;

wherein said crosslinker is psoralen.

4. A method for identifying and selecting a desired protein or nucleic acid molecule comprising:

providing an in vitro translation system;

providing at least two candidate mIRNA molecules, wherein at least one of said mRNA molecules is untranslatable beyond a particular codon selected from the group consisting of a nonsense codon, a codon for which tRNAs having an anticodon complementary thereto are absent or substantially depleted in said in vitro translation system, and a codon located on a 3' end of a translatable reading frame of said mRNA molecule;

translating at least two of said candidate mRNA molecules in said in vitro translation system to generate at least one translated protein, wherein a tRNA molecule accepts a peptide chain and holds said chain in a manner such that ribosomal peptidyl transferase cannot detach it because the message in subsequent codons is untranslatable;

linking at least one of said candidate mRNA molecules to its corresponding translated protein at or near said particular codon via said tRiNA molecule to form at least one cognate pair, wherein at least one of said candidate mRNA molecules is connected to said tRNA molecule by a crosslinker;

identifying one or more of said cognate pairs based upon the properties of said translated protein or said mRNA molecule, thereby identifying said desired protein or said desired nucleic acid molecule;

providing a plurality of said cognate pairs comprising said one or more identified cognate pairs, exposing said plurality of said cognate pairs to one or more binding agents; and selecting said desired protein or nucleic acid molecule based upon a reaction or lack of a reaction to said one or more binding agents;

wherein said crosslinker is an aryl azide.

* * * * *

UNITED STATES PATENT AND TRADEMARK OFFICE
CERTIFICATE OF CORRECTION

PATENT NO. : 7,410,761 B2
APPLICATION NO. : 10/847087
DATED : August 12, 2008
INVENTOR(S) : Richard B. Williams It is certified that error appears in the above-identified patent and that said Letters Patent is hereby corrected as shown below:

On Page 2, first column, line 18-21, under item 1993, please delete "Thionucleobases as Intrinsic Photoaffinity Probes of Nucleic Acid Structure and Nucleic Acid-Protein Interactions. Alain Favre, et al.; Journal of Photochemistry and Photobiology B: Biology, vol. 42, pp. 109-124, 1998.".

Title Pg, Item (56) OTHER PUBLICATIONS:

At page 2, right column, line 22, please delete "epidermidis" and insert --Epidermidis--, therefore.

At column 19, line 4, please delete "sane" and insert --same--, therefore.

At column 28, line 26, please delete "Eletrophoresis" and insert --Electrophoresis--, therefore.

At column 34, line 62, please delete "$A_{254nm}$" and insert --$A_{254}$nm--, therefore.

In Claim 3, please delete "niRNA" and insert --mRNA--, therefore.

In Claims 3, please delete "mIRNA" and insert --mRNA--, therefore.

In Claim 3, please delete "tRINA" and insert --tRNA--, therefore.

In Claim 4, please delete "mIRNA" and insert --mRNA--, therefore.

In Claim 4, please delete "rRiNA" and insert --tRNA--, therefore.

Signed and Sealed this

Fourteenth Day of April, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,410,761 B2  
APPLICATION NO. : 10/847087  
DATED : August 12, 2008  
INVENTOR(S) : Richard B. Williams It is certified that error appears in the above-identified patent and that said Letters Patent is hereby corrected as shown below:

On Page 2, first column, line 18-21, under item 1993, please delete "Thionucleobases as Intrinsic Photoaffinity Probes of Nucleic Acid Structure and Nucleic Acid-Protein Interactions. Alain Favre, et al.; Journal of Photochemistry and Photobiology B: Biology, vol. 42, pp. 109-124,1998.".

Title Pg, Item (56) OTHER PUBLICATIONS:

At page 2, right column, line 22, please delete "epidermidis" and insert --Epidermidis--, therefore.

At column 19, line 4, please delete "sane" and insert --same--, therefore.

At column 28, line 26, please delete "Eletrophoresis" and insert --Electrophoresis--, therefore.

At column 34, line 62, please delete "$A_{254nm}$" and insert --$A_{254}$nm--, therefore.

Column 60, in Claim 3, line 25, please delete "niRNA" and insert --mRNA--, therefore.

Column 60, in Claim 3, line 32, please delete "mIRNA" and insert --mRNA--, therefore.

UNITED STATES PATENT AND TRADEMARK OFFICE
CERTIFICATE OF CORRECTION

PATENT NO. : 7,410,761 B2
APPLICATION NO. : 10/847087
DATED : August 12, 2008
INVENTOR(S) : Richard B. Williams It is certified that error appears in the above-identified patent and that said Letters Patent is hereby corrected as shown below:

Column 60, in Claim 3, line 36, please delete "tRINA" and insert --tRNA--, therefore.

Column 60, in Claim 4, line 54, please delete "mIRNA" and insert --mRNA--, therefore.

Column 61, in Claim 4, line 3, please delete "rRiNA" and insert --tRNA--, therefore.

This certificate supersedes the Certificate of Correction issued April 14, 2009.

Signed and Sealed this

Fifth Day of May, 2009

JOHN DOLL
*Acting Director of the United States Patent and Trademark Office*